United States Patent
Laduca et al.

(10) Patent No.: US 11,826,524 B2
(45) Date of Patent: Nov. 28, 2023

(54) DEFLECTABLE CATHETER WITH COMPOUND CURVE ARTICULATION AND MATERIALS FOR THE SAME

(71) Applicant: QMAX, LLC, Santa Cruz, CA (US)

(72) Inventors: Robert C. Laduca, Santa Cruz, CA (US); Paul A. Laduca, Palm Harbor, FL (US); Frederich A. L. Alavar, San Jose, CA (US)

(73) Assignee: QMAX, LLC, Santa Cruz, CA (US)

( * ) Notice: Subject to any disclaimer, the term of this patent is extended or adjusted under 35 U.S.C. 154(b) by 294 days.

(21) Appl. No.: 15/891,024

(22) Filed: Feb. 7, 2018

(65) Prior Publication Data

US 2018/0344981 A1 Dec. 6, 2018

Related U.S. Application Data

(60) Provisional application No. 62/455,590, filed on Feb. 7, 2017.

(51) Int. Cl.
| | |
|---|---|
| *A61M 25/01* | (2006.01) |
| *A61L 29/00* | (2006.01) |
| *A61M 39/06* | (2006.01) |
| *A61L 29/06* | (2006.01) |
| *A61L 29/12* | (2006.01) |
| *A61M 25/00* | (2006.01) |

(52) U.S. Cl.
CPC ......... *A61M 25/0147* (2013.01); *A61L 29/00* (2013.01); *A61L 29/06* (2013.01); *A61L 29/126* (2013.01); *A61M 39/06* (2013.01); *A61M 39/0606* (2013.01); *A61M 39/0613* (2013.01); *A61M 25/005* (2013.01); *A61M 25/0045* (2013.01); *A61M 25/0113* (2013.01); *A61M 25/0136* (2013.01); *A61M 25/0138* (2013.01); *A61M 25/0144* (2013.01); *A61M 2025/0161* (2013.01); *A61M 2039/062* (2013.01); *A61M 2039/066* (2013.01); *A61M 2039/0673* (2013.01)

(58) Field of Classification Search
CPC .......... A61M 25/0045; A61M 25/0133; A61M 25/0136; A61M 25/0138; A61M 25/0147; A61M 2025/015; A61M 2025/0161; A61M 39/06; A61M 2039/062; A61M 25/0144; A61B 1/0051; A61B 1/0052; A61B 1/0057
See application file for complete search history.

(56) References Cited

U.S. PATENT DOCUMENTS

| | | | | |
|---|---|---|---|---|
| 4,838,859 | A | * | 6/1989 | Strassmann ........ A61B 1/00156 604/95.03 |
| 5,192,286 | A | * | 3/1993 | Phan .................... A61B 17/221 606/1 |
| 5,383,852 | A | * | 1/1995 | Stevens-Wright .......................... A61M 25/0136 604/95.04 |
| 5,388,568 | A | * | 2/1995 | van der Heide ..... A61B 1/0052 600/146 |

(Continued)

*Primary Examiner* — Kami A Bosworth
(74) *Attorney, Agent, or Firm* — Levine Bagade Han LLP

(57) ABSTRACT

Deflectable catheters, hemostasis valves, and materials for the same are disclosed. The deflectable catheters and hemostasis valves can be made at least partially, if not entirely, from a fluoroelastomer and ePTFE combination. A deflectable region of the catheters can be articulated to form simple and/or complex curves.

37 Claims, 16 Drawing Sheets

(56) References Cited

U.S. PATENT DOCUMENTS

| | | | | |
|---|---|---|---|---|
| 5,441,483 | A | * | 8/1995 | Avitall ............... A61B 18/1492 604/95.05 |
| 5,545,133 | A | * | 8/1996 | Burns ............. A61M 25/10187 604/99.04 |
| 5,882,333 | A | * | 3/1999 | Schaer .............. A61M 25/0144 604/95.01 |
| 6,033,378 | A | * | 3/2000 | Lundquist ......... A61M 25/0136 604/528 |
| 6,585,717 | B1 | * | 7/2003 | Wittenberger .... A61M 25/0138 604/523 |
| 2003/0130712 | A1 | * | 7/2003 | Smits ................ A61M 25/0138 607/116 |
| 2004/0044350 | A1 | * | 3/2004 | Martin ................. A61B 1/0057 606/139 |
| 2010/0228191 | A1 | * | 9/2010 | Alvarez ............ A61M 25/0105 604/95.01 |
| 2011/0065990 | A1 | * | 3/2011 | Verbeek ............. A61B 1/00135 600/142 |
| 2011/0206878 | A1 | * | 8/2011 | Sullivan ................. C08L 83/04 428/36.9 |
| 2013/0197306 | A1 | * | 8/2013 | Armand ............. A61B 17/3421 600/109 |
| 2014/0148759 | A1 | * | 5/2014 | Macnamara ...... A61M 25/0147 604/95.04 |
| 2016/0074625 | A1 | * | 3/2016 | Furnish ............. A61M 25/0136 604/95.04 |

\* cited by examiner

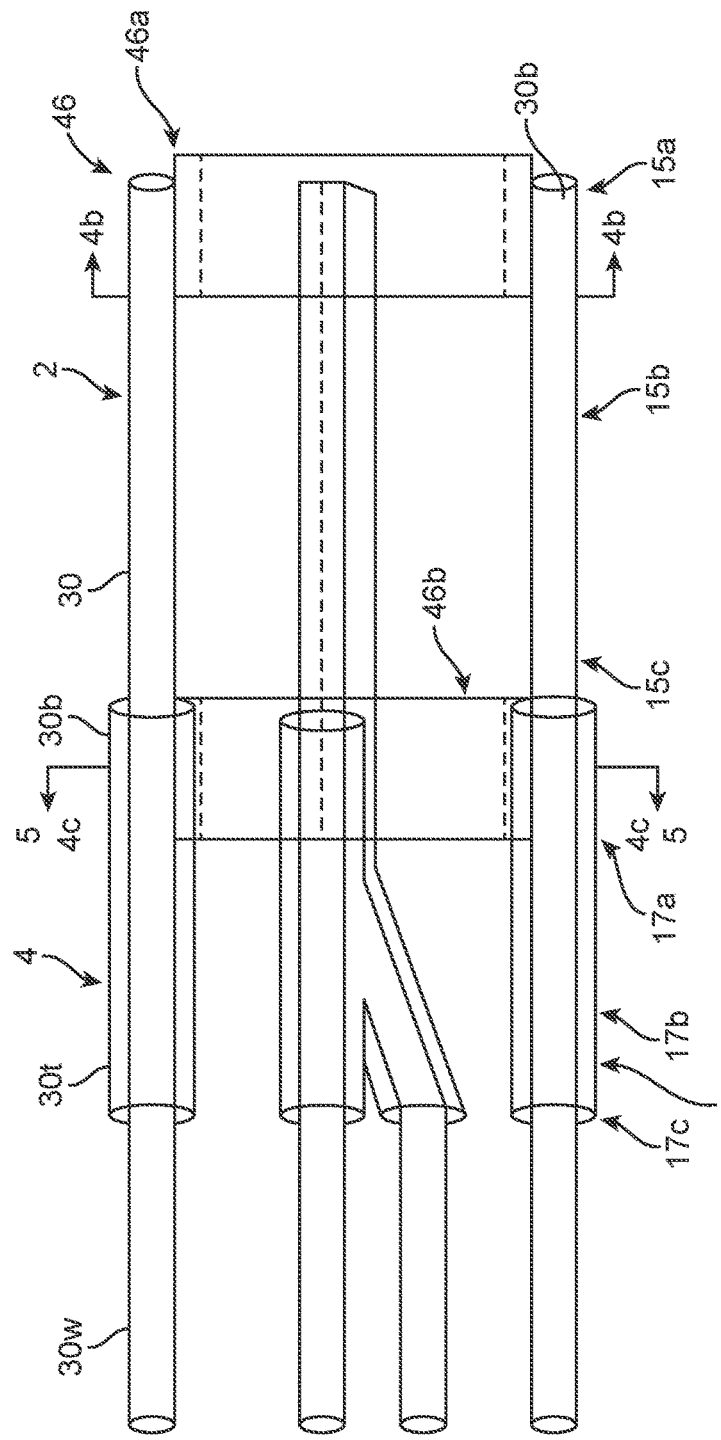
Fig. 4a
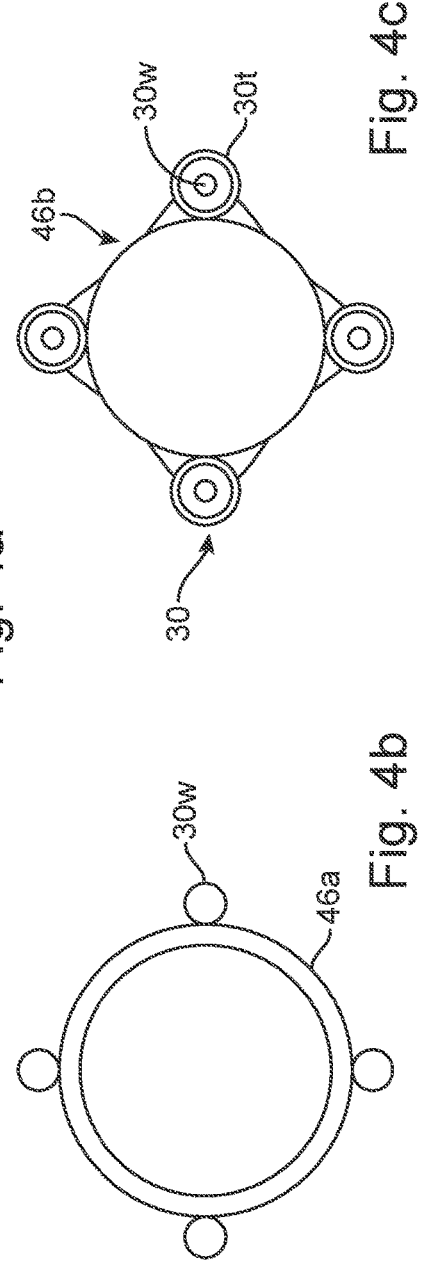
Fig. 4c
Fig. 4b

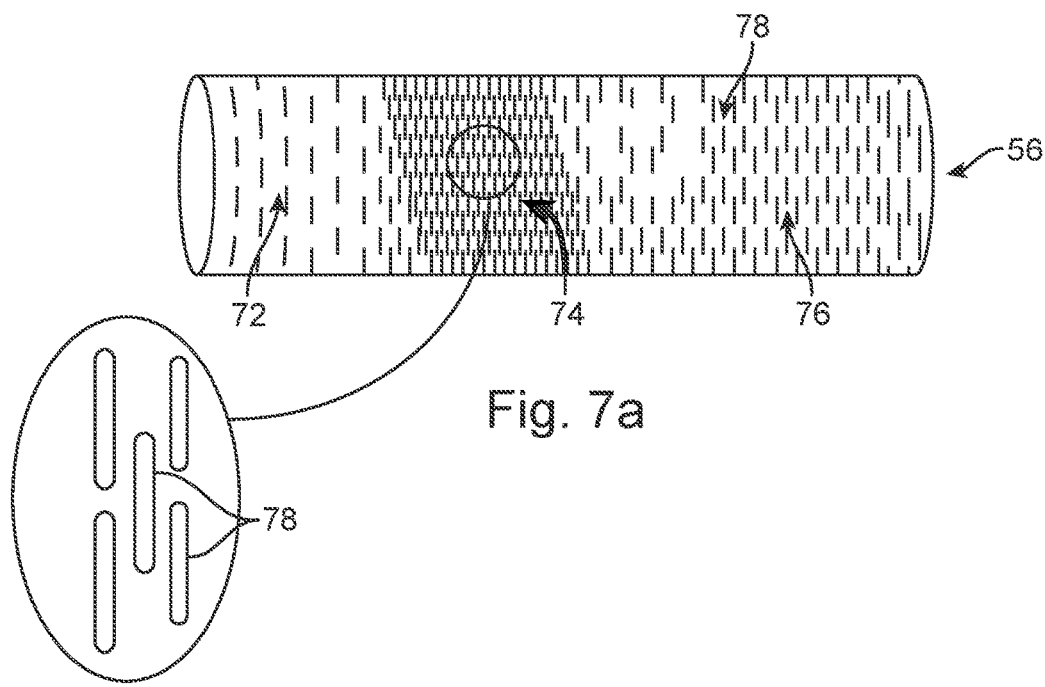
Fig. 7a
Fig. 7b
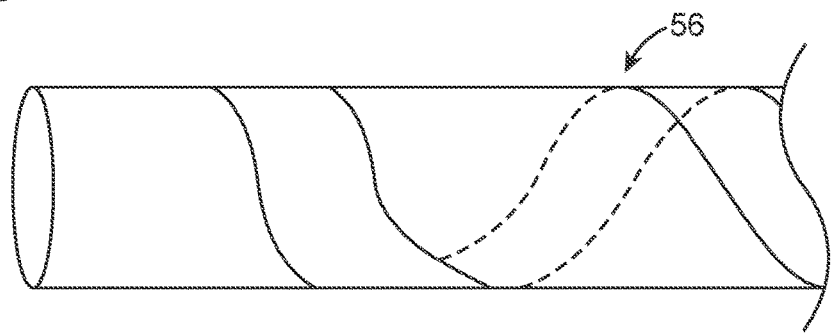
Fig. 7c
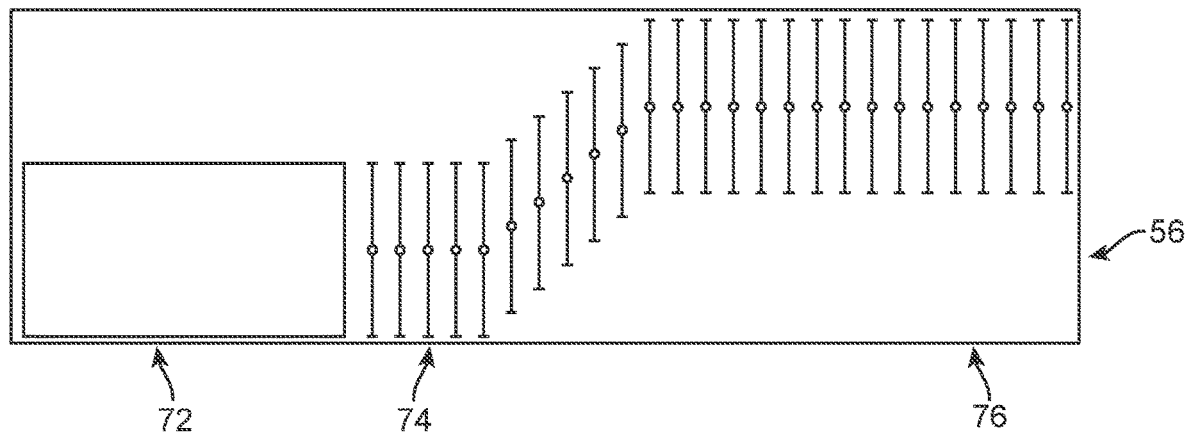
Fig. 7d

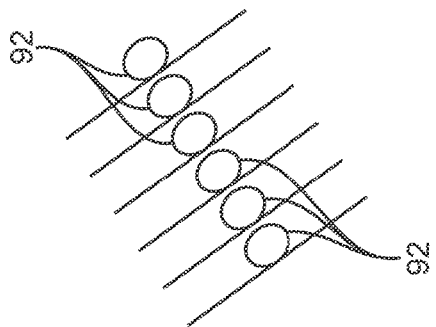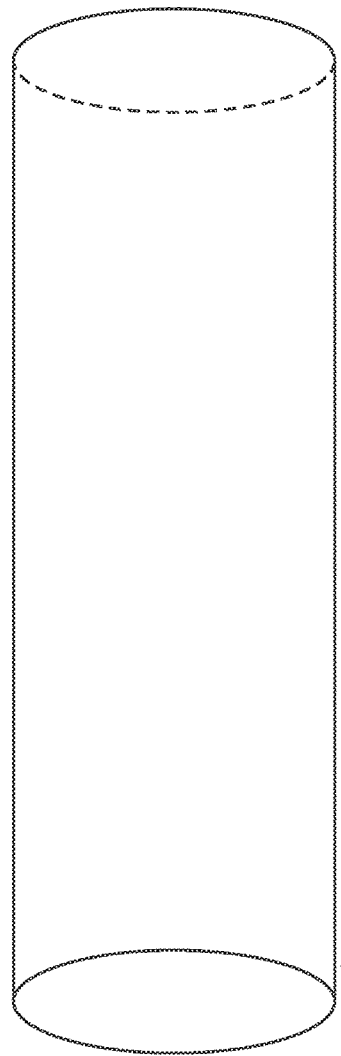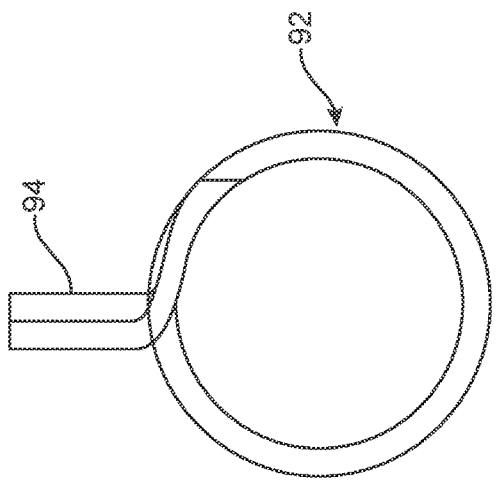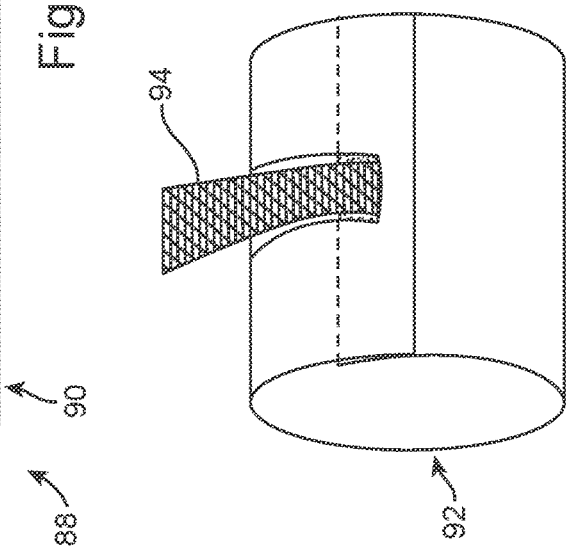

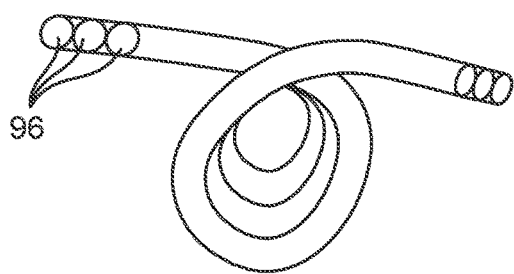
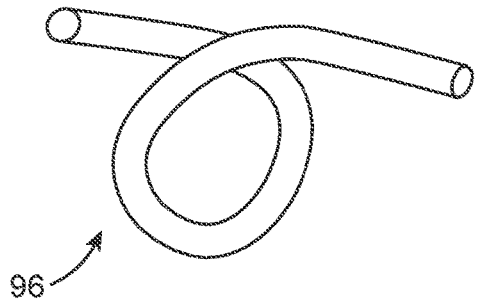
Fig. 8b1              Fig. 8b2
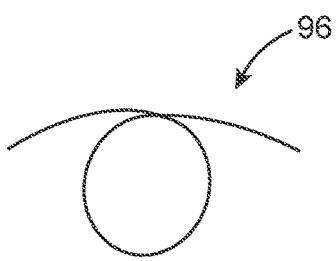
Fig. 8b3
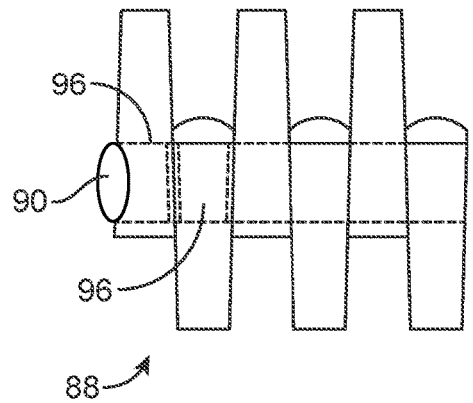
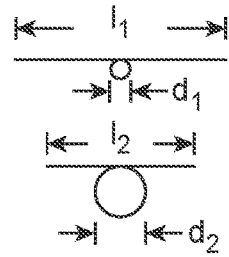
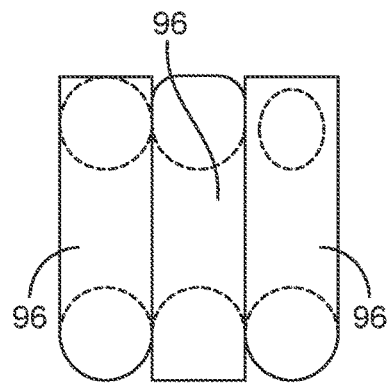
Fig. 8b4              Fig. 8b5              Fig. 8b6

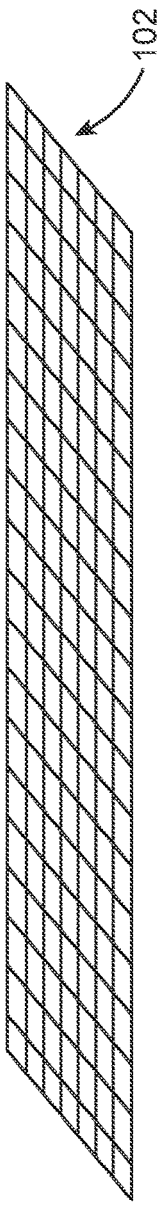
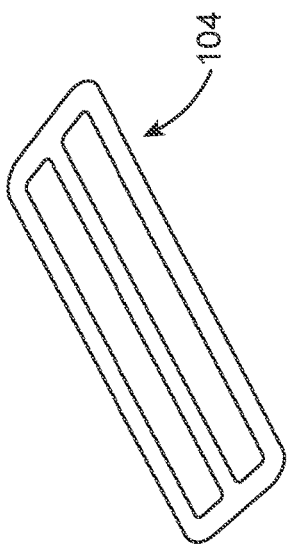
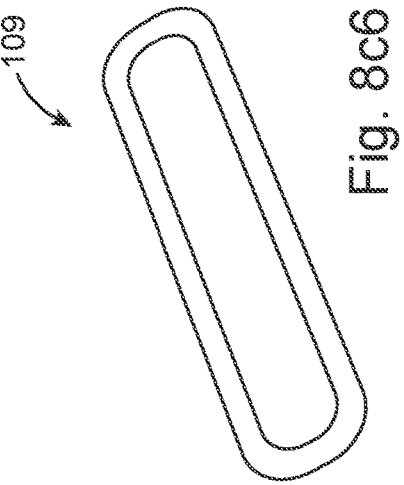
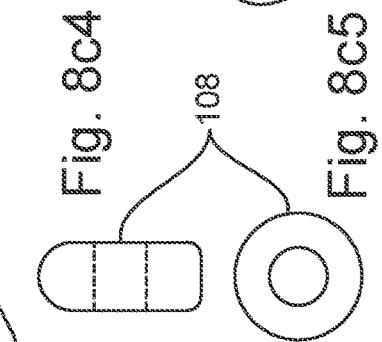
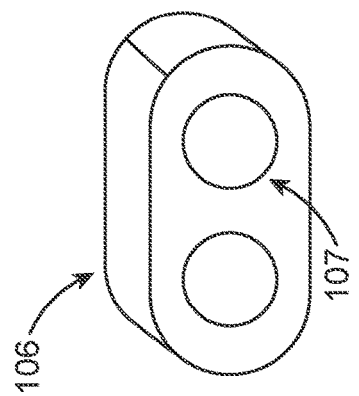
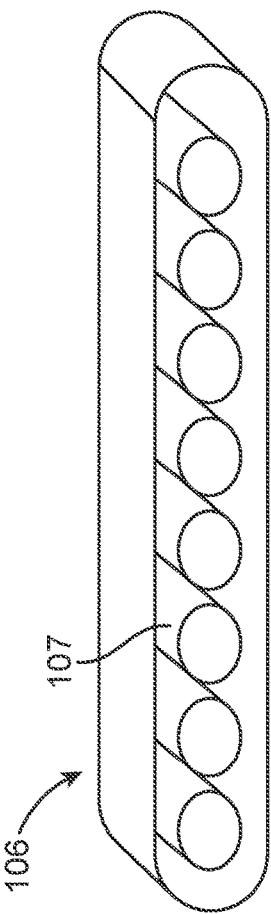
Fig. 8c1
Fig. 8c2
Fig. 8c3
Fig. 8c4
Fig. 8c5
Fig. 8c6
Fig. 8c7

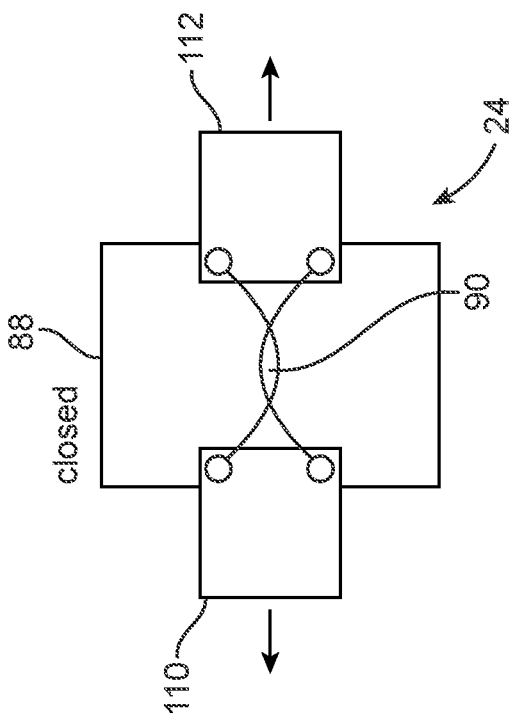
Fig. 8d1
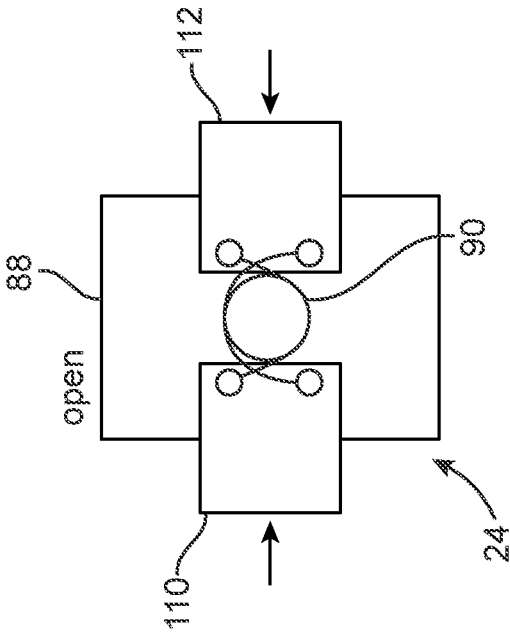
Fig. 8d2
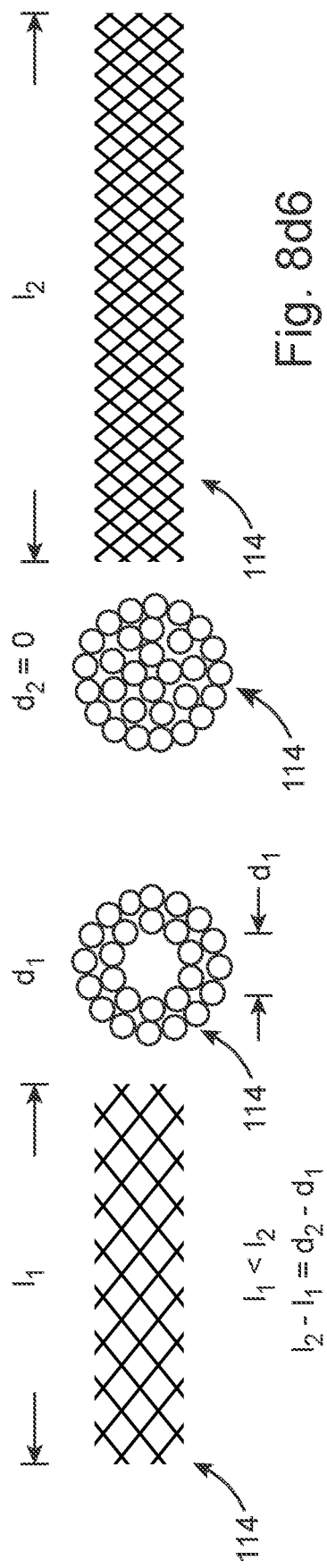
Fig. 8d3 Fig. 8d4 Fig. 8d5 Fig. 8d6

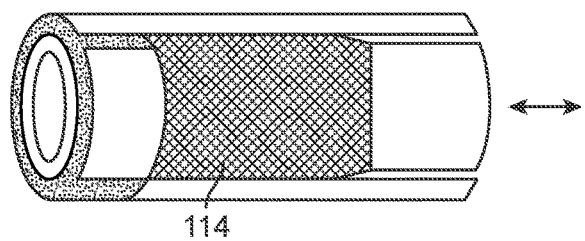
Fig. 8e1
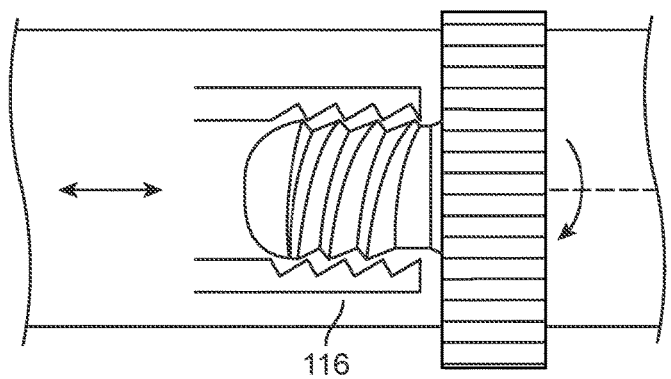
Fig. 8e2
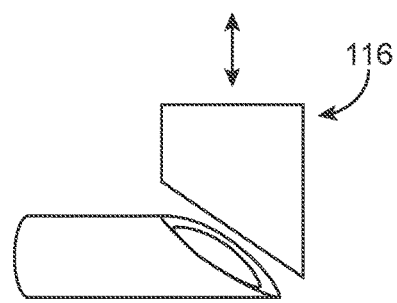
Fig. 8e3
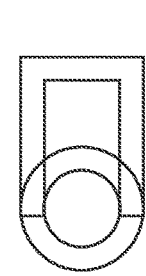
Fig. 8e5
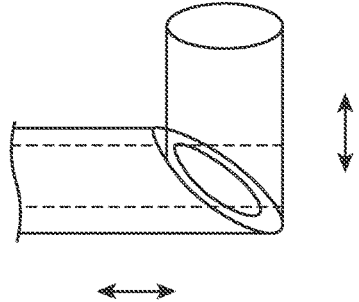
Fig. 8e4
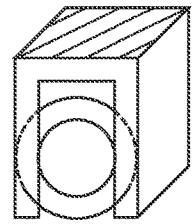
Fig. 8e6

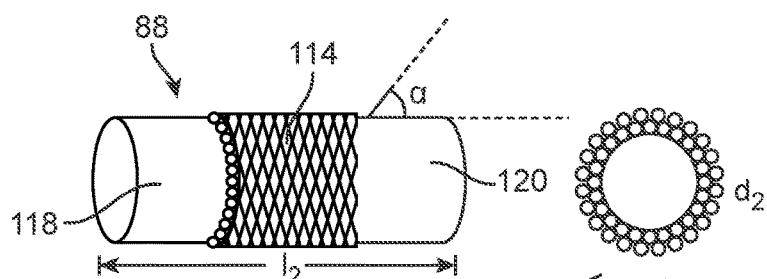
Fig. 8f1　　　　　　　　　　　　　Fig. 8f2
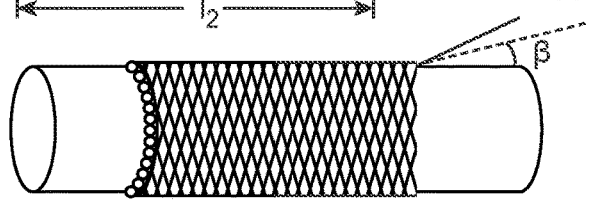
Fig. 8f3
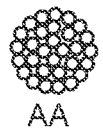
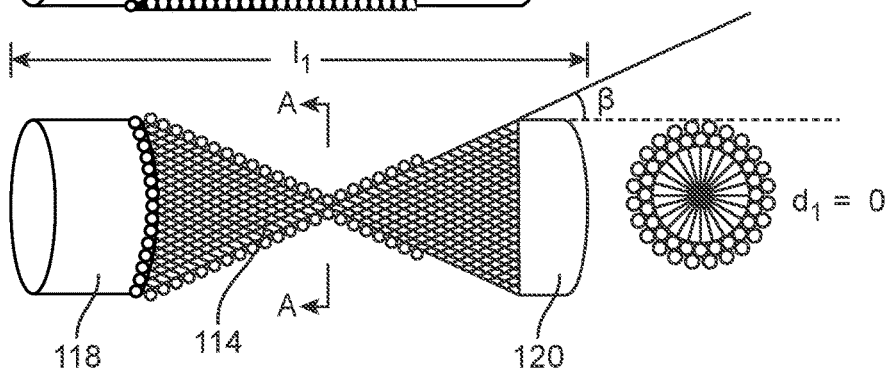
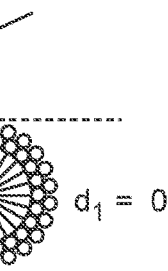
Fig. 8f4　　　　　Fig. 8f5　　　　　Fig. 8f6

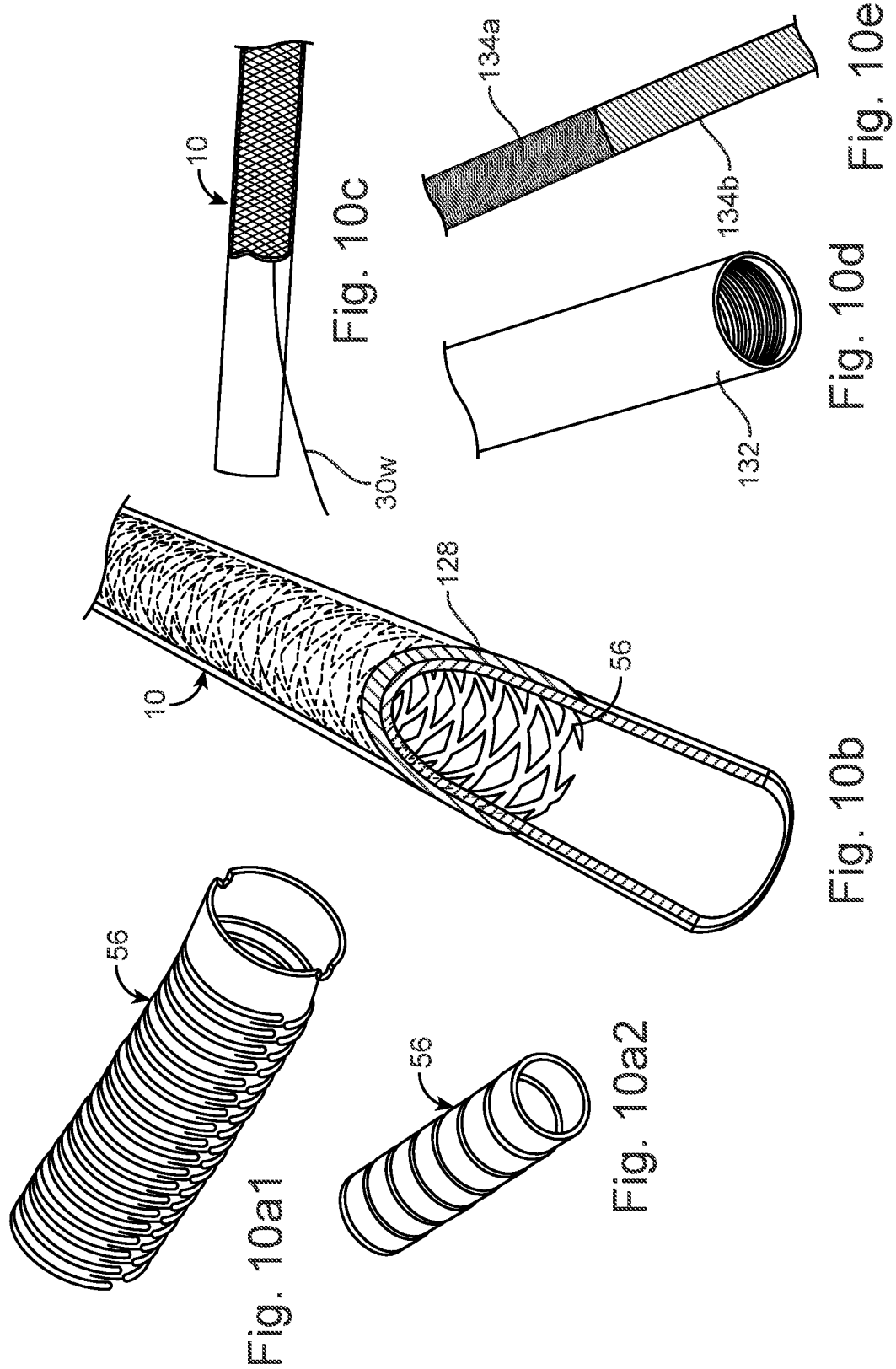

DEFLECTABLE CATHETER WITH COMPOUND CURVE ARTICULATION AND MATERIALS FOR THE SAME

CROSS-REFERENCE TO RELATED APPLICATIONS

This application claims priority to U.S. Provisional Application No. 62/455,590 filed Feb. 7, 2017, the content of which is incorporated herein by reference in its entirety.

SUMMARY

Deflectable catheters, hemostasis valves, and materials for the same are disclosed. The deflectable catheters and hemostasis valves can be made at least partially, if not entirely, from a fluoroelastomer and expanded polytetrafluoroethylene (ePTFE) combination. A deflectable region of the catheters can be articulated to form simple and/or complex curves.

BACKGROUND OF THE INVENTION

A deflectable catheter that can be articulated into a compound curve can be useful to navigate tortuous vessels. The applications where a compound curve with precise navigation and stability to maintain the tip of the catheter at the target location within the anatomy include the delivery of implantable devices such as heart valves, stents, stent grafts, therapeutic agents, drugs, biological materials, scaffolds, pace maker leads, and the like. The ability to precisely control the tip of the catheter can be important in the delivery of therapy to repair heart valves or other cardiac structures such as patent foramen ovalae, septal defects, atrial appendage, removal of clot, excision of tissue, biopsy, organ dissection and removal, tumor ablation and surgery to remove cancer and other growths, ovarian cyst removal, and more.

Since each of these applications can require a different pathway to navigate, the particular device requirements for the flexibility and lengths of deflection curves as well as the relative location of compound curves, catheter tubing is often designed to be specific to the path within the anatomy to reach the target location within the body. For example, to access the mitral valve, one such approach would be to enter the body at the femoral vein and navigate through the inferior vena cava to the right atrium and across the septum to reach the left atrium. The particular range of compound curves that the catheter must take require both a flexible and trackable catheter that has generally a more flexible distal portion and a more stiff proximal portion with a range and orientation of specific deflection curves to steer the catheter tip into the proper target and once there provide a dimensionally stable tubing configuration to allow the procedural steps to repair the target or for the delivery or removal of implantable devices. The deflectable catheter disclosed herein can provide greater versatility and flexibility than both conventional catheters conventional deflectable catheters.

Many applications, such as balloon catheters, vascular sheaths and introducers, require low friction surfaces on their internal and external surfaces. Improved materials for these and many other catheter and endoscopic applications are needed. A composite material with high flexibility, toughness, and good recovery after deformation strains, and that has properties typical of an elastomer with a coefficient of friction similar to PTFE, the polymer with the lowest coefficient which is non-elastomeric, is desired. The combination of an elastomeric fluoropolymer with ePTFE can advantageously have these properties.

The fluoroelastomer and ePTFE composite material can have a low coefficient of friction and low modulus of elasticity. This particular combination of physical properties are important in interventional procedures where device requirements for torque, compressive strength, flexibility, tensile strength, elongation, and fatigue are all material factors upon which the success of the procedure depends.

Currently, low modulus, low durometer, flexible elastic materials have a tacky high friction surface. High friction materials can lead to higher application of forces that can result in material and/or device failure. The fluoroelastomer and ePTFE composite material disclosed herein provides a low friction surface that is also elastic.

BRIEF DESCRIPTION OF THE DRAWINGS

FIG. 4a illustrates a cross section of a variation of the deflectable distal region of FIG. 1 without the catheter shaft.

FIG. 4b illustrates a cross section of the deflectable distal region of FIG. 4a taken along line 4b-4b.

FIG. 4c illustrates a cross section of the deflectable distal region of FIG. 4a taken along line 4c-4c.

FIG. 7a illustrates a variation of a laser cut hypotube.

FIG. 7b illustrates a magnified view of the laser cut hypotube of FIG. 7a.

FIG. 7c illustrates a variation of a laser cut hypotube with a helical slot pattern.

FIG. 7d illustrates a variation of a flattened hypotube.

FIGS. 8a1-8a4 illustrate a variation of a hemostasis valve.
FIGS. 8b1-8b6 illustrate a variation of a hemostasis valve.
FIGS. 8c1-8c7 illustrate a variation of a hemostasis valve.
FIGS. 8d1-8d6 illustrate a variation of a hemostasis valve.
FIGS. 8e1-8e6 illustrate a variation of a hemostasis valve.
FIGS. 8f1-f6 illustrate a variation of a hemostasis valve.

FIGS. 10a1 and 10a2 illustrate variations of a tube.

FIG. 10b illustrates a variation of a jacket.

FIG. 10c illustrates a variation of a pull wire arrangement.

FIG. 10d illustrates a variation of a liner.

FIG. 10e illustrates a variation of a multi-durometer catheter.

DETAILED DESCRIPTION

Figure 1:
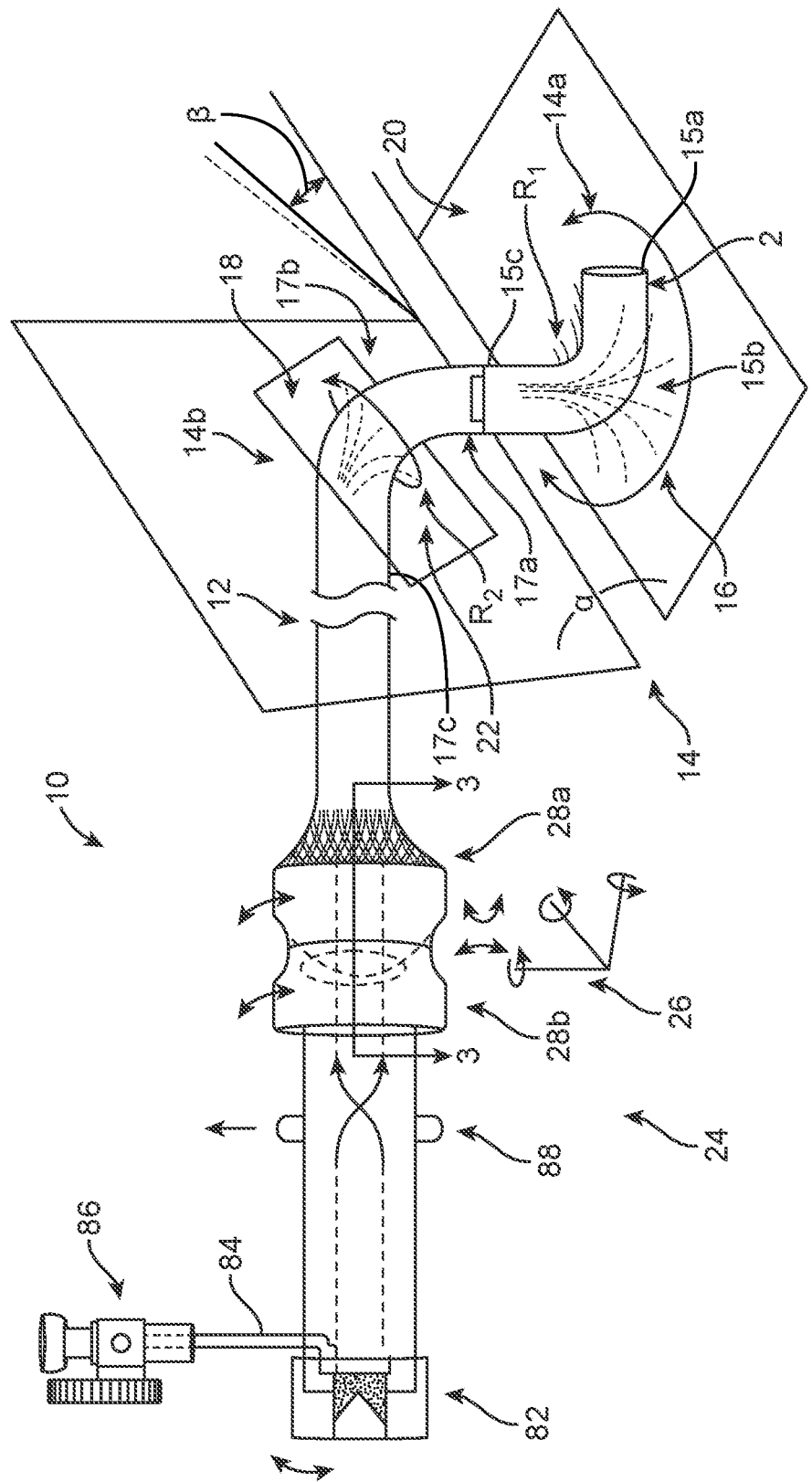
FIG. 1 illustrates a variation of a catheter having a deflectable distal region.

FIG. 1 illustrates a variation of a catheter 10 having a shaft 12 with a deflectable distal region 14. The deflectable distal region 14 can form a simple and/or a compound curve (e.g., one, two, three or more curves). For example, as shown in FIG. 1, the deflectable distal region can form a compound curve with a first curve 16 and a second curve 18. Although the deflectable portion 14 in FIG. 1 is located at a distal region of the catheter, the deflectable portion 14 can be located anywhere along the length of the catheter, including the distal region and/or one or more other sections of the shaft 12 proximal the distal region 14.

The deflectable distal region 14 can have one or more deflection portions. For example, FIG. 1 illustrates that the deflectable region can have a first deflection portion 14a and a second deflection portion 14b. More or less deflection portions are also appreciated (e.g., three or more deflection portions). Each deflection portion can form one or more curves. As shown in FIG. 1, the first deflection portion 14a can form a first curve (e.g., first curve 16) and the second deflection portion 14b can form a second curve (e.g., second curve 18).

The shaft 12 of the catheter 10 can include the deflectable portion 14. For example, as shown in FIG. 1, the first and second deflection portions 14a, 14b can be an integral part of the catheter shaft 12. However, it will be appreciated that the deflectable portion 14 of the catheter 10 can be two or more discrete shafts, or deflectable portions, joined together.

Although not illustrated in FIG. 1, one or more spacers can be positioned adjacent to one or more of the deflectable portions of the catheter. For example, a spacer can be positioned between the first and second deflection portions 14a, 14b. The one or more spacers can be configured to resist deflection. For example, the spacer can be made of material that is less elastic (more stiff) than a neighboring deflectable portion. As another example, the spacer can be a reinforcement structure (e.g., wire, wire mesh, braid, tube, etc.) that is embedded in the wall of the catheter 10 adjacent to one or more of the deflection portions (e.g., between the first and second deflection portions 14a, 14b). The one or more spacers can have any suitable length. The shaft 12 can have one or more predefined bends/curves in the shaft 12.

Each deflection portion can have a first end, a middle segment, and a second end. The second end can be articulated relative to the first end such that the middle segment bends when the second end is articulated. For example, the first deflection portion 14a can have a first end 15a, a middle segment 15b, and a second end 15c, and the second deflection portion 14b can have a first end 17a, a middle segment 17b, and a second end 17c. As shown in FIG. 1, the first end, middle segment, and second end of each of the deflection portions can be relative positions on the catheter shaft 12, for example, relative positions on the distal region 14 of the catheter shaft 12. The first end, middle segment, and second end of each of the deflection portions can be relative positions on one or more discrete shafts assembled together. As will be described in further detail below, the first end of each of the deflection portions (e.g., first ends 15a, 17a) can correspond to where a control element (e.g., a pull element, a pull wire and/or a pull tube, among others) is welded or otherwise attached to the catheter shaft (e.g., at a pull structure such as a pull ring). The first end of a deflection portion can coincide with the second end of another deflection portion. For example, the first end 17a of the second deflection portion 14b can coincide with the second end 15c of the first deflection portion 14a, or otherwise be nearly or substantially adjacent to it. As another example, the first end 17a of the second deflection portion 14b can be spaced apart from the second end 15c of the first deflection portion with, for example, a spacer.

Each deflection portion can be independently or otherwise selectively articulated (e.g., relative to another deflection portion). For example, the first and second deflection portions 14a, 14b in FIG. 1 can be independently articulated relative to one another to form the first and second curves 16, 18. In this way, the catheter tip 2 can be articulated independently of a selectively activated/formed secondary curve (e.g., curve 18). The deflection portions can be selectively articulated together and/or separately from one another. For example, the first and second curves 16, 18 can be selectively articulated together and/or separately from one another. Each deflection portion can be selectively activated from one or more separate controls that are configured to bend or otherwise articulate the deflectable region 14 into one or more simple and/or complex curves (e.g., the compound curve formed by first and second curves 16, 18).

The first end 15a of the first deflection portion 14a (e.g., the catheter tip 2) can be articulated in a 360 degree circumference with a bend radius $R_1$. The first end 17a of the second deflection portion 14b can be articulated in a 360 degree circumference with a bend radius $R_2$. As shown in FIG. 1, the first end 15a of the first deflection portion 14a can define a first plane of rotation 20 and the first end 17a of the second deflection portion 14b can define a second plane of rotation (not shown). The first deflection portion 14a can define a first plane of deflection (not shown) and the second deflection portion 14b can define a second plane of deflection 22. Each plane of deflection can be, for example, a plane that is orthogonal to the shaft 12 at the midpoint of its respective bend. For example, the first plane of deflection can be orthogonal to the shaft 12 at the midpoint of the first curve 16 and the second plane of deflection 22 can be orthogonal to the shaft 12 at the midpoint of the second curve 18. FIG. 1 illustrates that the first plane of rotation 20 can form an angle α between with the second plane of deflection 22. The second plane of rotation can be located proximal to the distal tip 2 so that the deflectable portion of the shaft 12 can be articulated with a control to form compound curve (e.g., curves 16, 18).

Each deflection portion can be articulated with a control such that it can form one or more curves in one or more articulation planes. The deflection portions can be bidirectional (two-way) and/or unidirectional (one-way) in each plane of articulation. The deflection portions can be bidirectional (two-way) and/or unidirectional (one-way) in each plane of articulation relative to, for example, an axial centerline. For example, the first and second deflection portions 14a, 14b in FIG. 1 can be bidirectional such that the curves 16, 18 in FIG. 1 can curve 180 degrees in reverse so that the first ends 15a, 17a point in the opposite directions shown.

The neutral position of the deflectable region 14 can be linear and/or curved. The first end 15a of the first deflection portion 14a can be articulated such that the first deflection portion 14a can form one or more curves in one or more planes of articulation. The first end 17a of the second deflection portion 14b can be articulated such that the second deflection portion 14b can form one or more curves in one or more planes of articulation. The deflectable portions can be articulated in one, two, three, four, or more planes of articulation, although any number of articulation planes is appreciated (e.g., 10 or less and 10 or more). The one or more planes of articulation can intersect, for example, at an axial center line of the shaft 12. The planes of articulation can be angled relative to one another at 90 degrees or less. For example, two planes of articulation can be orthogonal to one another and/or can be angled 45 degrees to one another. Other angles between articulation planes, more or less, are also appreciated.

The deflectable portions can have the same number and/or a different number of articulation planes relative to one another. For example, the first deflection portion 14a can be articulated in four planes of articulation and the second deflection portion 14b can be articulated in two planes of articulation. By way of example, a third deflection portion could be articulated in two, three, or four planes of articulation, among any other number. Any combination of articulation planes is appreciated. Any angle permutation of articulation planes is appreciated, both relative to a single deflection portion and/or relative to different deflection portions. For example, the first deflection portion 14a can be articulated in a first set of orthogonal planes and the second deflection portion 14b can be articulated in a second set of orthogonal planes offset 45 degrees relative to the first set of orthogonal planes. FIG. 1 illustrates that the first and second deflection portions 14a, 14b can each have one, two, three, and/or four planes of articulation.

The deflectable portions (e.g., first and second deflection portions 14a, 14b) can be selectively articulated without in their respective articulation planes without having to rotate the shaft 12. When the shaft 12 is rotated through an angular displacement, the articulation planes can rotate through the same angular displacement.

Handle

FIG. 1 illustrates that the catheter 10 can have a handle 24 having one or more controls 26, one or more hemostasis valves 88, and a valve 82. A flush tube 84 can be connected to the handle 24. A flush device 86 can be connected to the flush tube 84.

The handle 24 can be configured to deflect the deflectable portions of the shaft 12. For example, the handle 24 can be operatively coupled to the deflectable portions of the shaft 12, for example, to the first and second deflection regions 14a, 14b. One or more controls can be used to deflect the deflectable portion into a curved shape (e.g., the compound curve shown in FIG. 1). The one or more controls can be operatively coupled to the deflectable portions of the shaft 12 via one or more control elements (e.g., a pull element, a pull wire, a pull tube, a connection, a pull structure, etc.). The one or more control elements can be selectively manipulated with one or more controls to bend or otherwise articulate the deflectable region 14 into one or more simple and/or complex curves. The deflectable region 14 can be articulated into a compound curve without a force from outside the catheter being applied to it (e.g., a force from a vessel wall). For example, the one or more controls can be used to articulate the deflectable region 14 into a compound curve without a force from outside the catheter being applied to it (e.g., a force from a vessel wall).

FIG. 1 illustrates that the handle 24 can have one or more controls 26, such as first and second handle knobs 28a, 28b. The control 26 can be operatively coupled to the deflectable portions of the shaft 12, for example, to the first and second deflection regions 14a, 14b. The control 26 can be a ball and socket gimbal joint, and can be operatively coupled to the deflectable portions of the shaft 12 via one or more control elements (e.g., a pull element, a pull wire and/or a pull tube). Each control element can have a first end and a second end. The first ends of the one or more control elements can be coupled to a control (e.g., control 26) and the second ends of the one or more control elements can be coupled to a deflectable portion of the shaft 12 (e.g., the first and/or second deflection portions 14a, 14b). As described in further detail below, the second ends of the one or more control elements can be coupled to one or more pulls structures (e.g., one or more pull rings) integrated with or otherwise attached to the deflectable region (e.g., deflectable region 14) of the shaft 12.

One or more control elements can be coupled to the first and second knobs 28a, 28b. For example, two control elements can be coupled to the first knob 28a and two control elements can be coupled to the second knob 28b. Other numbers of control elements, more or less, can be coupled to the control 26 and/or to one or more additional controls 26, for example, one or more additional handle knobs. Each knob can be manipulated (e.g., physically and/or via an auditory command) to deflect a deflectable portion of the shaft 12 into a curved shape. Each knob can be rotated and/or translated (i.e., manipulated). The first knob 28a can be used to articulate the first deflection portion 14a into one or more curved shapes. The first knob 28a can be used to articulate the second deflection portion 14b into one or more curved shapes. The second knob 28b can be used to articulate the first deflection portion 14a into one or more curved shapes. The second knob 28b can be used to articulate the second deflection portion 14b into one or more curved shapes.

In this way, the control 26 can be used to selectively apply tension to the one or more control elements by, for example, manipulating the control 26, and thereby articulate the deflectable portions of the shaft 12 into one or more curved shapes. The control 26 can selectively apply tension to the one or more control elements by actuating the first and/or second knobs 28a, 28b relative to one another and/or relative to the handle 24. As described above, the control 26 can have a ball and socket joint. The first knob 28a can have a partially spherical surface that can be received by a cup or socket feature of the second knob 28b (i.e., the first knob 28a can be a ball knob and the second knob 28b can be a socket knob). The first knob 28a can be rotated to displace one or more control elements via a clockwise and/or a counter-clockwise rotation and the second knob 28b can be rotated to displace its two coupled control elements via a clockwise and/or a counterclockwise rotation.

A longitudinal dimension between the first and second knobs 28a, 28b can be increased or decreased when the first and/or second knobs 28a, 28b are rotated relative to one another and/or relative to the handle 24. The longitudinal displacement that results between the first and second knobs 28a, 28b can result in a change in tension in one or more control elements, which can in turn deflect the deflectable portion of the shaft 12 (e.g., the deflectable distal region 14). An angular dimension between the first and second knobs 28a, 28b can be increased or decreased when the first and/or second knobs 28a, 28b are rotated relative to one another and/or relative to the handle 24. The angular displacement that results between the first and second knobs 28a, 28b can result in a change in tension in one or more control elements, which can in turn deflect the deflectable portion of the shaft 12 (e.g., the deflectable distal region 14).

The one or more controls 26 can be locked or otherwise remain in position when the deflectable region 14 is articulated into the desired simple and/or compound curves.

Handle and Control Elements

Figure 2:
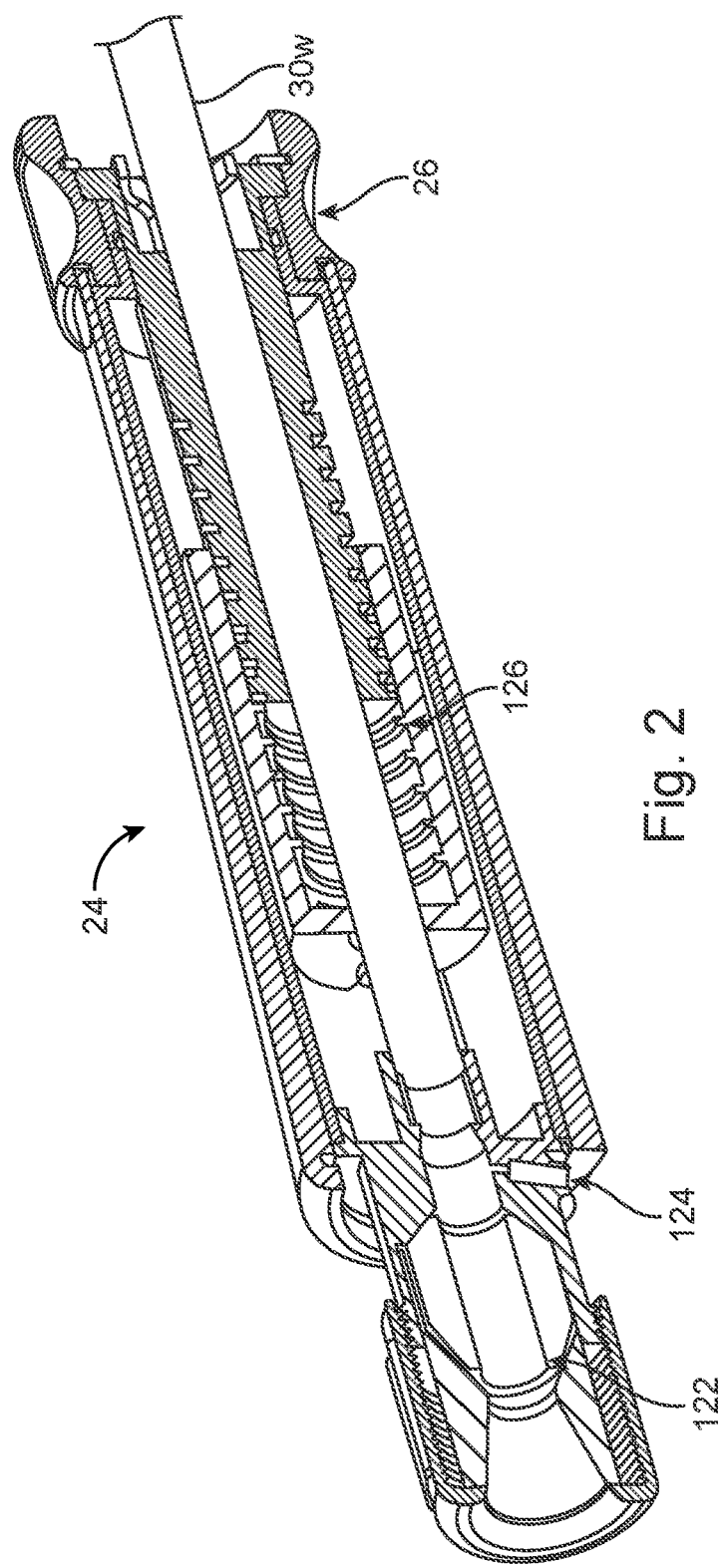
FIG. 2 illustrates a cross section of a variation of a catheter handle.

FIG. 2 is a longitudinal cross section of a variation of a two-way deflectable distal tip handle (e.g., handle 24). FIG. 2 illustrates that the knobs of the one or more controls 26 (e.g., knobs 28a, 28b) can each have a helical threaded control element termination slide that moves to independently pull the control elements into the handle assembly 24 when the knob is rotated clockwise and/or counterclockwise. The control elements can be pull elements, pull wires, and/or pull tubes, among any other suitable control element. For example, the control 26 in FIG. 2 (e.g. knob 28a or knob 28b) can tension one of two (or more) pull wires 30w while the other pull wire 30w is not in tension. FIG. 2 also illustrates that the handle 24 can have a hemostasis valve 122. The valve 122 can be on the proximal end of the handle 24, and can have a rotating cap to compress an internal elastomer ring to actively close the internal diameter. FIG. 2 also illustrates that the handle 24 can have a channel 124 for flush port tubing. FIG. 2 also illustrates that the handle 24 can have a slideable pull wire termination block 126 having helical thread.

Figure 3:
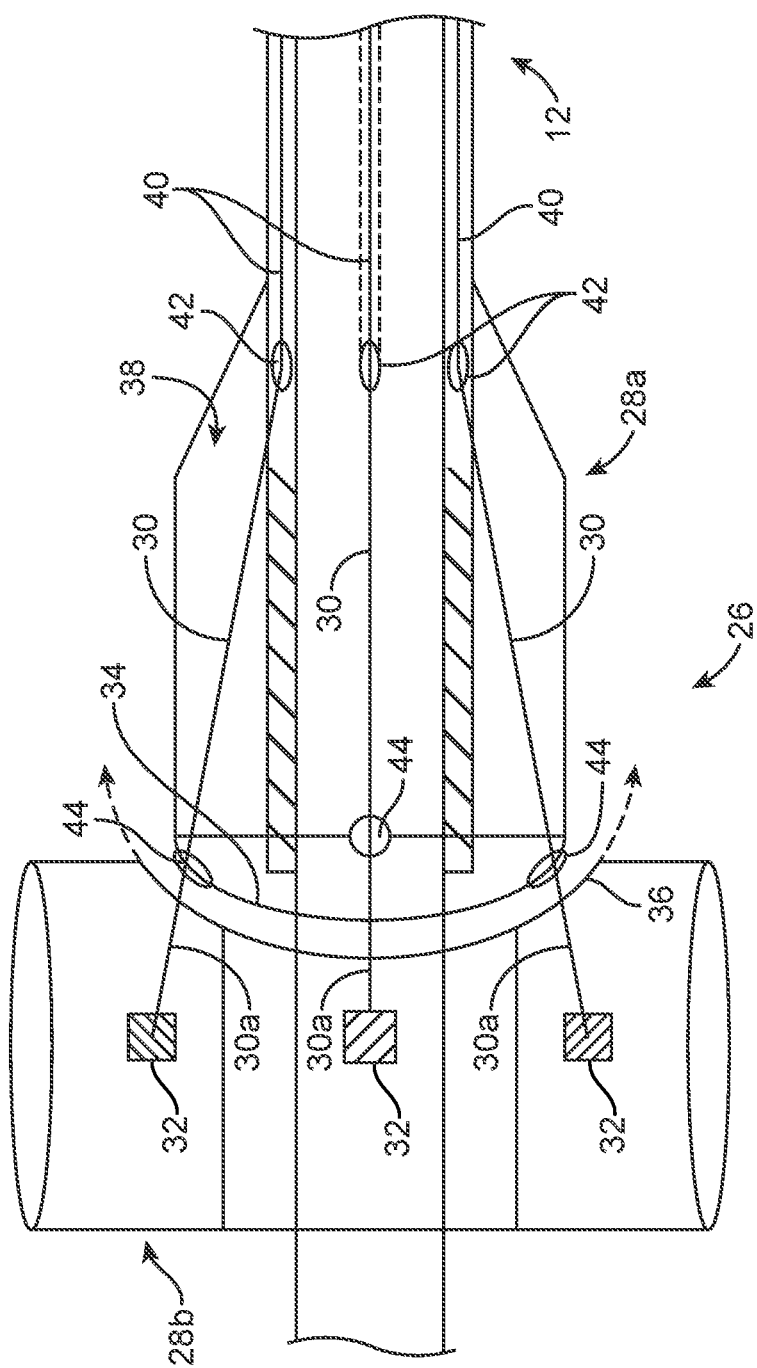
FIG. 3 illustrates a cross section of the catheter of FIG. 1 taken along line 3-3.

FIG. 3 is a cross sectional view of FIG. 1 taken along the lines 3-3. FIG. 3 illustrates various aspects of the shaft 12, the one or more control elements 30, and the first and second knobs 28a, 28b (also referred to as ball and socket knobs 28a, 28b). As shown, the catheter 10 can have four pull wires 30. The first ends 30a of the four pull wires 30 can terminate in and/or at connections 32. The connections 32 can be crimps, welds, and/or other attachment means. The connections 32 (e.g., pull wire crimps) can be attached to and/or integrated with the socket knob 28b. The control 26 in FIG. 3 can have any suitable number of control elements 30 and connections 32. For example, the control 26 can have four pull wires 30 attached to four corresponding connections 32 (only three are shown due to the cross section view). However, other numbers of pull wires 30 and/or connections 32, more or less, are also appreciated, such as four pull wires and four pull tubes, among other permutations.

The ball and socket knobs 28a, 28b can have ball and socket surfaces 34, 36, respectively, such that the socket surface 36 can receive or otherwise mate with the ball surface 34. The first knob 28a can have a hub 38. The first and second knobs 28a, 28b can be rotatably attached to the shaft 12 (e.g., the hub 38 of the first knob 28a can be rotatably attached to the shaft 12).

FIG. 3 illustrates that the shaft 12 can have one or more lumens 40 located in the wall of the shaft 12. The one or more lumens 40 can form one or more exit ports 42 in the wall of the shaft 12. As shown, the shaft 12 can have four lumens and exit ports 40, 42 (only three are shown due to the cross section view). Other numbers of lumens 40 and/or exit ports 42, more or less, are also appreciated. The exit ports 42 can be skived. The exit ports 42 can be located such that the control elements 30 exit the shaft 12 and are slide-ably disposed within the hub 38 and exit on the ball surface 34 at four orthogonal locations 44 (only three shown due to cross section view).

FIG. 4a illustrates a cross section of the deflectable distal region 14 of FIG. 1 in a linear configuration before the first and/or second deflection portions 14a, 14b are deflected into the compound curve having curves 16, 18. The shaft 12 is shown transparent for purposes of illustration but is still included in the description below. As shown, the second ends 30b of the control elements 30 can be attached to a wall of the shaft 12 via one or more pull structures 46 (e.g., pull rings). The one or more pull rings 46 can be attached to and/or integrated with a wall of the shaft 12. For example, the deflectable portion can have a first pull ring 46a and a second pull ring 46b. Other numbers of pull structures, more or less, are also appreciated.

The first pull ring 46a can be positioned on or otherwise attached to a wall of the shaft 12, for example, at or near the first end 15a of the first deflection portion 14a. The second pull ring 46b can be positioned on or otherwise attached to a wall of the shaft 12, for example, at or near the first end 17a of the second deflection portion 14b. The first ends 15a, 17a of the first and second deflection portions 14a, 14b can correspond to where the first and second pull rings 46a, 46b are located. The first and second pull rings 46a, 46b can be positioned within the deflectable distal region 14 at any suitable location. One or more spacers can be positioned between and/or adjacent to the first and second pull structures 46a, 46b.

FIG. 4a illustrates that the control elements can be pull wires 30w and/or pull tubes 30t. One or more pull wires 30w can be slide-ably disposed within a pull tube 30t. The pull wires 30w can be attached to the first pull ring 46a and the pull tubes 30t can be attached to the second pull ring 46b. The distal pull wires 30w can be attached to the distal pull ring 46a by means of welding, solder, loop, or any other fixation method. The proximal pull tubes 30t can be attached to the proximal pull ring 46b by means of welding, solder, loop, or any other fixation method. An advantage of this configuration is that both sets of control elements 30 (e.g., the set of pull wires 30w and the set of pull tubes 30t) can be located directly on the circumferential centerlines for the orthogonal bending moments as shown in the cross sections in FIGS. 4b and 4c (taken along the lines 4b-4b and 4c-4c in FIG. 4a). These circumferential centerlines can lie on one or more of the articulation planes described above. Although the pull tubes and pull wires 30t, 30w in FIG. 4a are shown truncated, it will be appreciated that the pull tubes and wires 30t, 30w can extend the length of shaft 12 to their respective first ends 30a. The pull wires 30w can be slide-ably disposed inside the pull tubes 30t along at least a portion of the length of the pull tube 30t. For example, the pull wires 30w can be slide-ably disposed inside the pull tubes 30t from the first end 30a of the pull tubes 30t to the second end 30b of the pull tubes 30t. As another example, the pull wires 30w can be slide-ably disposed inside one or more sections of the pull tubes 30t (e.g., one, two, three, or more sections) between the first end 30a of the pull tubes 30t to the second end 30b of the pull tubes 30t. The pull wires 30w can exit the pull tubes 30t at or near the second pull ring 46b. Other exit locations are also appreciated.

In another variation, a first set of control elements 30 can be attached to the first pull ring 46a and a second set of control elements 30 can be attached to the second pull ring 46b such that each control element is adjacent to the orthogonal centerlines shown in FIGS. 4b and 4c (i.e., not exactly coincident with the circumferential centerlines shown in FIGS. 4b and 4c). However, this arrangement can have the undesired effect of introducing an offset between the deflection planes of the distal pull wires 30w that can be attached to the first pull ring 46a and the proximal pull wires 30w that can be attached to the second pull ring 46b. The result of the offset is that the deflectable region 14 may not deflect both curves (e.g., curves 16, 18) perfectly in plane with one another and/or relative to one another. That said, an advantage of having the distal and proximal pull wires 30w arranged side-by-side rather than in the wire-tube configuration is that the wall thickness of the shaft 12 can be reduced in the side-by-side configuration as compared to the wire-tube configuration.

To address the disadvantage of the proximal pull tubes 30t adding to the wall thickness of the shaft 12, a flat wire braid, a high tensile polymer braid, and/or a woven tape can be used instead of one or more of the pull tubes 30t. Each of these structures can have a lumen like the lumens of the pull tubes 30t shown in FIGS. 4a-4c, but rather than having a large diameter lumen sufficient to maintain the required pull wire tension forces, these structures can have flatter lumens with an equivalent amount of cross sectional area of wire as the pull tubes 30*t*. These structures can therefore provide a tensile strength that is equivalent to the pull tubes 30*t*, but can advantageously do so in a lower profile configuration to reduce the wall thickness of the composite tube 12 (also referred to as the shaft 12).

The shaft 12 can have a hydrophilic coating on the outer surface to improve its ability to navigate tortuous vessels. For example, the shaft 12 can be coated with a HYDAK® coating from Biocoat, Inc. Horsham, PA.

The catheter tip 2 can have a balloon to seal and/or secure the device during use.

The distal region 14 and/or other parts of the shaft 12 can have one or more radiopaque markings.

The deflectable portion of the catheter shaft 12 (e.g., the deflectable distal region 14) can be made of a combination of fluoroelastic material and expanded polytetrafluoroethylene (ePTFE). The fluoroelastic and ePTFE materials can be fused together. The fused composite material can advantageously have a low friction surface that is also elastic. For example, the composite material can have the friction of PTFE, but have an elastic modulus. The composite material can have an elongation to yield of 200% or higher and simultaneously exhibit high tensile strength and low friction. Other elongation to yield percentages, more or less, are also appreciated. The composite material can have both high heat stability and high chemical resistance, which can allow for the reusability of the device by facilitating re-sterilization by either steam autoclave and/or chemical processes. The shaft 12 can be made partly and/or entirely from the fluoroelastomer and ePTFE combination. The composite material can form the internal and/or external surfaces of the shaft 12. For example, the composite material can form the inner and outer diameter of the shaft 12, such as, for example, the inner and outer surfaces of the distal region 14. The fluoroelastic and ePTFE composite material and the process for making it will be described in further detail below. The composite material can be fused to higher modulus melt process-able TFE based fluoropolymer thermoplastics such as, for example, ETFE, EFEP, and FEP to create a catheter shaft 12 with variable stiffness along its length.

The deflectable catheter tubing 12 can be reinforced with a polymer and/or metallic braid, a coil, or a laser cut tubing. The composite shaft 12 can be fused with other materials as well, including block polyether amide, nylon, polyurethane, and other melt process-able thermoplastics.

The deflectable distal region 14 can be formed by (1) locating one or more pull structures along the length of the catheter shaft 12, (2) varying the modulus of the tubing 12 along the length of the catheter shaft 12, and/or (3) varying the compressibility of the material along the length of the catheter shaft 12, among other any other suitable method. For example, a pre-defined laser cut pattern of metallic or polymeric tubing can be embedded or otherwise disposed in the wall of the deflectable section 14 so that one or more controls 26 can be manipulated to articulate the deflectable section 14 in three dimensions, where the primary and secondary curves of articulation (e.g., curves 16, 18) can be controlled independently of each other.

Any catheter shaft can have and/or be made from any of the structures and/or materials described herein. For example, any catheter shaft can have and/or be made from the fluoroelastic composite material (i.e., the fluoroelastomer and ePTFE combination). Any portion of any catheter shaft, including its full length, can have and/or be made from the fluoroelastomer and ePTFE composite material. For example, the fluoroelastomer and ePTFE composite material can form any portion of a catheter having a straight segment, any portion of a catheter having a curved segment, any portion of a bendable catheter (e.g., a flexible catheter), any portion of a non-bendable catheter (e.g., a stiff catheter), any portion of a deflectable region of a catheter (e.g., deflectable region 14), and/or any portion of a non-deflectable region of a catheter (e.g., the region proximal to deflectable region 14), including their full lengths and/or one or more segments along their lengths. The fluoroelastomer and ePTFE composite material can form any portion of any catheter capable of forming one or more simple curves. The fluoroelastomer and ePTFE composite material can form any portion of any catheter capable of forming one or more compound curves. Any of these catheters can have any of the reinforcement structures and/or other materials described herein.

Figure 5:
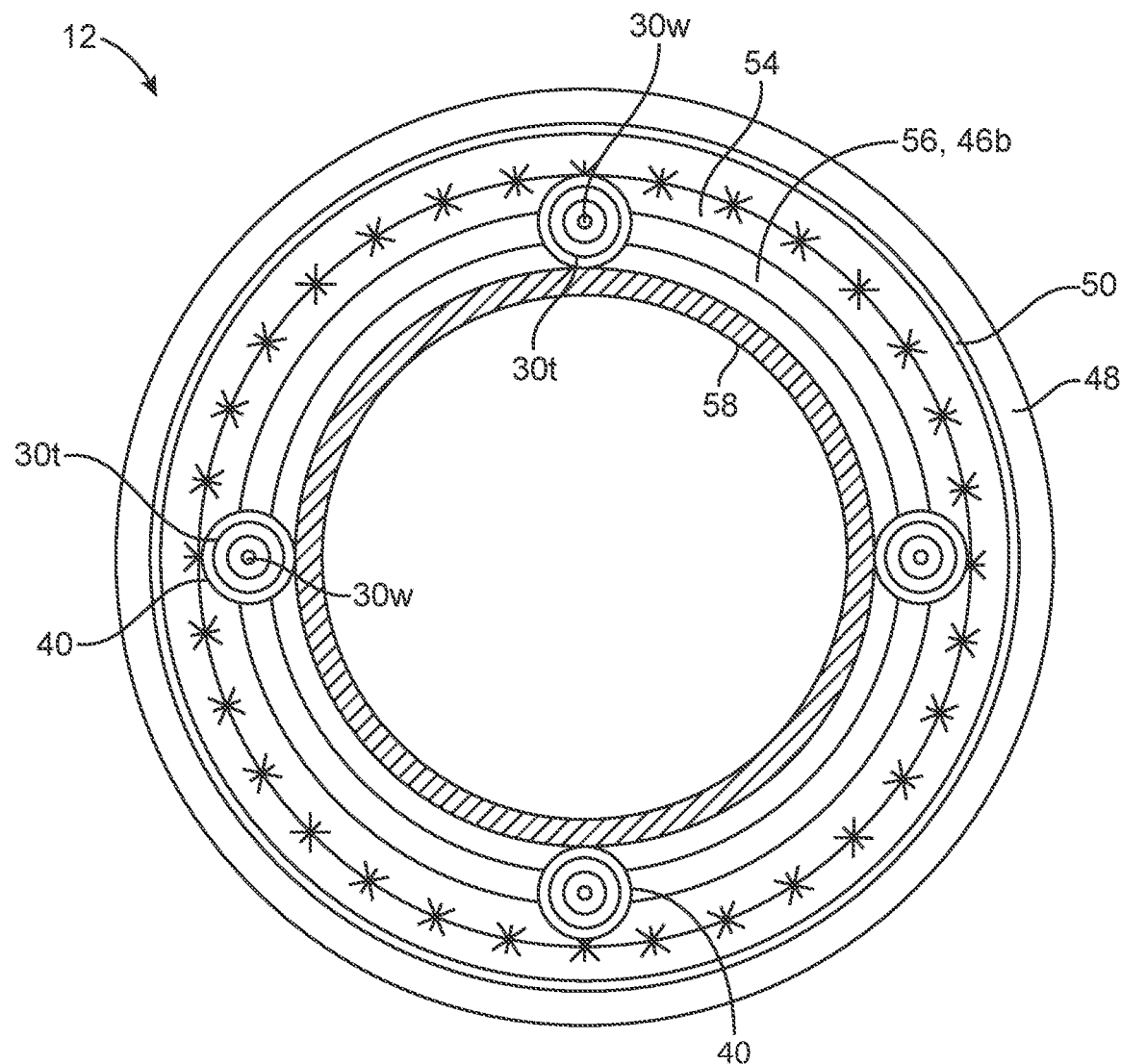
FIG. 5 illustrates a cross section of the deflectable distal region of FIG. 4a taken along line 5-5 with the catheter shaft.

Referring now to FIG. 5, this figure illustrates a cross section of the deflectable distal region 14 of FIG. 4*a* taken along the line 5-5 with the catheter shaft 12 now shown. As described above, the shaft 12 can be a composite material. The shaft 12 can have one or more reinforcement structures. FIG. 5 illustrates that the shaft 12 can have an outer layer 48, a coil 50, a braid 52, a middle layer 54, a tube 56, and/or a liner 58. The coil, braid, and tube 50, 52, 56 can advantageously reinforce the shaft 12. As shown, the outer layer 48 can be a flexible material (e.g., a flexible polymer) that encapsulates the coil 50, and the coil 50 can overlap or otherwise encapsulate the braid 52. The coil 50 and/or the braid 52 can be embedded in the outer layer 48 and/or the middle layer 54. The coil 50 can be a tightly wound, zero gap metal coil. The braid 52 can be made from stiff and/or flexible filament elements (e.g., metal wires). The tube 56 can be a pull structure (e.g., pull ring 46*b*) and/or a laser cut hypotube. Other suitable coils, braids, and tubes 50, 52, 56 are appreciated. The outer and middle layers 48, 54 can be made from the same material and/or from different materials. The liner 58 can be made from the same material and/or from different materials than the outer and/or middle layers 48, 54. For example, one or more of the outer layer 48, middle layer 54, and the liner 58 can be made from the fusion of fluoroelastic material and ePTFE material.

One or more lumens 40 can be defined within the wall (e.g., within the wall thickness) of the composite shaft 12. The one or more lumens 40 can extend from the one or more proximal exit ports 42 (e.g., see FIG. 3) to one or more distal exit ports (not shown). The one or more distal exit ports can be located in the deflectable distal region 14 of the shaft 12 and/or before it. As shown in FIG. 5, the proximal pull ring 46*b* can be securely attached to the pull tube 30*t*. The pull tubes 30*t* can be disposed within the lumens 40. One or more of the lumens 40 can be lined with PTFE or other materials that have a higher melting point than the encapsulating material (i.e., the material of the shaft 12 that surrounds the lumens 40, for example, the middle layer 54 which can be made from, for example, the fusion of a fluoroelastomer and ePTFE material). A suitable lining material for the lumens 40 will have a low coefficient of friction to reduce control element (e.g., pull wire and/or pull tube) sliding forces and to prevent the encapsulating material of the lumen jacket from intruding into the lumen 40 during the fusing process of fabricating the composite shaft 12. The middle layer 56 can define the lumen jacket of the lumen 40. FIG. 5 illustrates that a distal pull wire 30*w* can be disposed in the pull tube 30*t* (e.g., in the center of the pull tube 30*t*). Other materials/structures than a PTFE lining for the lining of the lumens 40 can include a stainless steel or nitinol hypotube, a braid reinforced polyimide tubing, PEEK, PEN, PET, polysulfone, PFA, ETFE, LCP, or other high modulus, high melt point polymer tubing.

Figure 6:
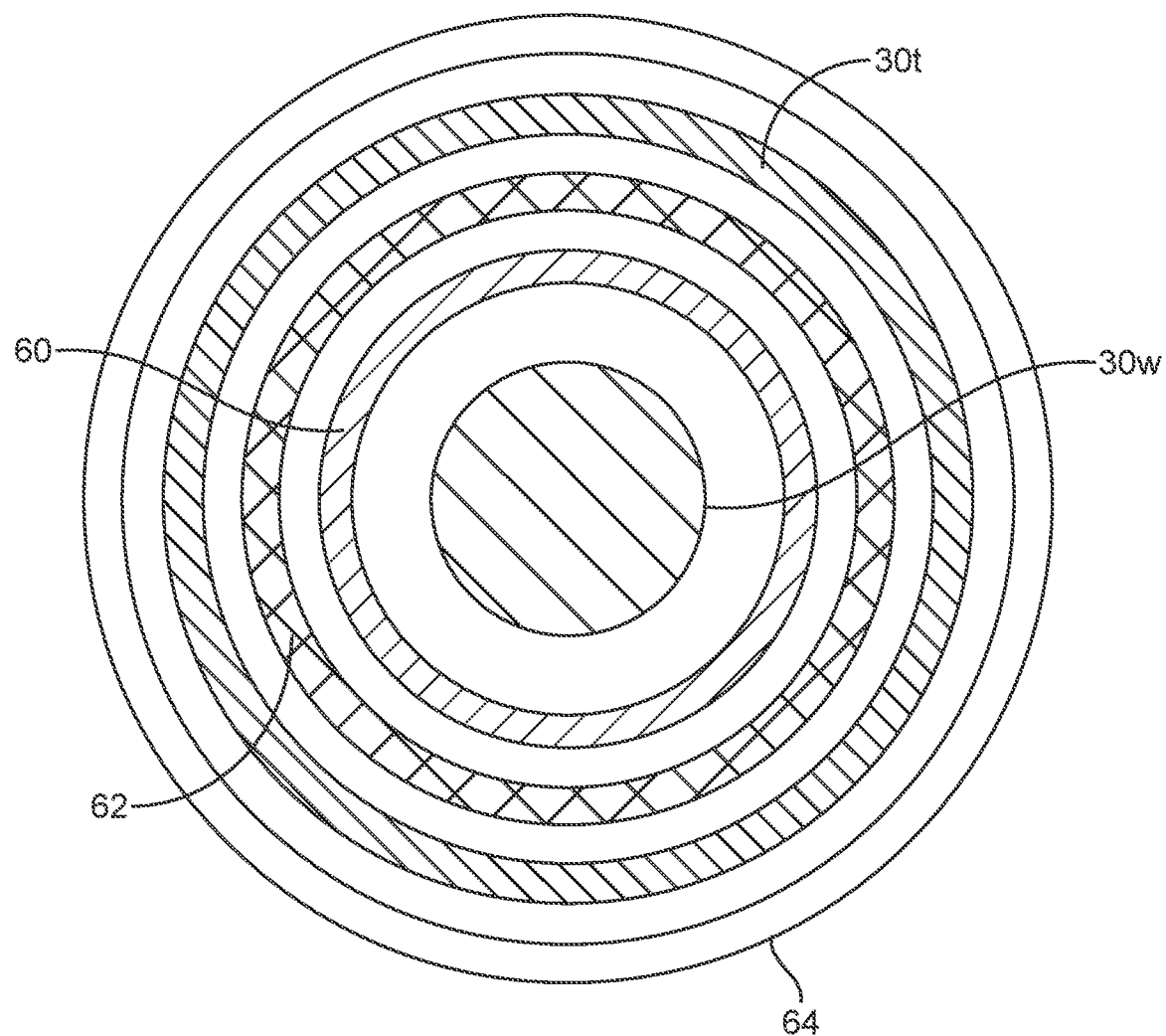
FIG. 6 illustrates a close-up of a lumen of FIG. 5 with a pull wire disposed in a pull tube.

FIG. 6 illustrates a close-up of a lumen 40 of FIG. 5 with a pull wire 30w disposed in a pull tube 30t. As shown, the pull wire 30w can be disposed within a hollow member 60. The hollow member 60 can be flexible and/or incompressible. The hollow tube 60 can have a proximal end attached to a control hub (e.g., the hub 38 of FIG. 3). The hollow tube 60 can have a distal end attached to a pull structure (e.g., the distal pull ring 46a). For illustrative purposes, the proximal end of the hollow member 60 is shown transparent in FIG. 3.

The hollow tube 60 can translate/transmit a compressive force from the hub 38 to the distal portion of the pull wire 30w (e.g., the second end of the pull wire 30w). In this way, the tube 60 can move within a lumen 40 (not shown) except at each end where the tube 60 can be secured with a pre-compression load at the time of attachment (e.g., a slight pre-compression load). A compressive force can be applied to the proximal end of the hollow tube 60 from a connection 32 (e.g., the crimp 32 in FIG. 3) through the incompressible connection between the first and second knobs 28a, 28b (e.g., between the curved mating surfaces of the ball and socket knobs 28a, 28b). The compressive force applied to the tube 60 via the hub 38 can propagate through the tube 60 within the shaft 12 to the distal end of the hollow tube 60. In this way, each hollow member 60 can resist the tension force applied to the distal pull ring by tensioning its corresponding distal pull wire 30w (e.g., the pull wires 30w of FIG. 5).

The hollow tube 60 can be a coil. For example, the hollow member 60 can be a stainless steel coil with a tight wind. The hollow member 60 can be made from PTFE with an embedded reinforcement wire (e.g., an embedded longitudinal reinforcement wire). The embedded wire can increase the compressive strength of the PTFE. As another example, the hollow member 60 can be made from a hollow multifilar cable tube with a thin high modulus polymer jacket. The thin high modulus polymer jacket can increase compression strength of the hollow multfilar cable tube. As yet other examples, the hollow member 60 can be made from a stainless steel, titanium, or nitinol hypotube and/or a metal braid reinforced with polyimide, PEEK, PEN, PET, polysulfone, PFA, ETFE, LCP, or other high modulus material. The tubing 60 can have laser cut pattern to provide more flexibility while still providing high compressive resistance for isolation of the deflection bending moments between the distal deflection segment and the proximal deflection segment (e.g., between the first and second deflection portions 14a, 14b). The material and/or structure of each of the hollow tubes 60 can be the same and/or different from one another.

The hollow tube 60 can be slide-ably disposed within a lumen of a tube 62. The tube 62 can be hollow. The tube 62 can be a PTFE or other low friction material that has a higher melting point than the encapsulating jacket material 54 (e.g., see FIG. 5). The high temperature resistance of the tube 62 can isolate the molten encapsulating jacket material (e.g., middle layer 54) from intruding onto the surface of the incompressible hollow tube 60. This can advantageously allow the hollow tube 60 freedom to slide-ably move relative to the wall of the composite shaft 12, and thereby translate or otherwise propagate the compressive force from the proximal end of the hollow tube 60 to the distal pull structure 46a. Both ends of the hollow member 60 can be secured such that the hollow member 60 can move relative to the encapsulating material 54 and the wall of the composite shaft 12 (e.g., the entire wall thickness of the composite shaft 12).

The pull wire 30w and the hollow tubes 60, 62 can be disposed within a lumen of the pull tube 30t. The pull tube 30t can be a hollow tube that resists elongation when an axial tensile force is applied to it. The pull tube 30t can slide within a lumen of an outer tubing 64. The pull tube 30t can slide linearly within a lumen of an outer tubing 64. The pull tube 30t can slide within and along a center axis the outer tubing 64. The outer tubing 64 can be flexible and/or incompressible. The outer tubing 64 can resist compression applied to it from the proximal pull ring 46b (e.g., see FIG. 4) when a tensile force is applied to the pull tube 30t by actuating, for example, the handle knob 28b. The proximal deflection curve bending moment can be isolated from the more proximal section of the composite shaft 12 so that the deflection force is applied (e.g., preferentially applied) to the location of the proximal deflection section 14b. This is similar to how the distal pull wire 30w and the hollow incompressible member 60 isolate the deflection bending moment of the distal deflection segment 14a from the proximal deflection segment 14b.

Laser Cut Hypotube

FIG. 7a illustrates a variation of a laser cut hypotube (e.g., laser cut hypotube 56). As shown, the laser cut hypotube 56 can have one or more zones. For example, the hypotube 56 can have first, second, and third zones 72, 74, 76. Each zone can have cuts 78 (also referred to as windows or slots). Other numbers of zones, more or less are also appreciated. FIG. 7b illustrates a partial magnified view of cuts 78 of a portion of the hypotube 56 of FIG. 7a. The hypotube 56 can provide the distal region 14 of the shaft 12 with bending characteristics and can advantageously prevent the distal region 14 from kinking when articulated into one or more simple and/or compound curves.

Each zone of the hypotube can have one or more cut patterns. The hypotube zones can have different bending characteristics due to the number of cuts 78, the density of the cuts 78, the relative location of the cuts 78 (e.g., relative to one another and/or relative to one or more other zones), and/or the dimensions of the cuts 78 (e.g., the length and/or width of the cuts 78). For example, the pattern of cuts 78 in zone 72 can be less dense than the pattern of cuts 78 in zone 74. As a result, the hypotube 56 can be more flexible in zone 74 than in zone 72. For example, the hypotube 56 can have two way flexibility in zone 74 (e.g., for bending left and right in an articulation plane) and less than two way flexibility in zone 72 (e.g., one way flexibility).

The denser pattern in zone 74 can helically wrap around a circumferential portion of the hypotube 56, up to and including all the way around the circumference. This can advantageously allow the hypotube 56 to form a compound curve relative to the bending plane of the pattern of cuts 78 in zone 72. For example, the pattern of cuts 78 in zone 74 can be helical for ¼ to ½ of the tube circumference. This can advantageously create an offset to the neutral axis of the tube such that the distal portion pattern of cuts 78 in zone 76, which can be cut to provide all-way uniform bending flexibility (also referred to as omnidirectional bending flexibility), can be independently deflected from the bending curve in zone 72 and the bending curve of the tube in zone 74. As another example, FIG. 7c illustrates a variation of a laser cut hypotube with a helical slot pattern that extends around the full circumference of the tube.

The hypotube 56 can be a reinforcement structure embedded within the shaft 12. The hypotube 56 can provide reinforcement to the shaft 12. For example, the hypotube 56 can be disposed within the deflectable distal region 14 of the shaft 12. However, it will be appreciated that the laser cut tube 56 can be disposed or otherwise embedded within and/or along any length of the catheter shaft 12, including the entire length of the shaft 12 or less (e.g., within and/or along one or more sections of the shaft 12).

The outer diameter of the catheter shaft 12 with an embedded hypotube (e.g., hypotube 56) can range from approximately 0.020" to 0.600" and the wall thickness can range from approximately 0.006" to 0.100". Table 1 below (next page) lists minimum bend radii for various outer diameters and wall thicknesses.

TABLE 1

Various dimensions and properties.

| Outer diameter | Typical Wall thickness | Minimum bend radius |
| --- | --- | --- |
| 0.020" | 0.006"-0.008" | 0.1" |
| 0.060" | 0.008"-0.018" | 0.14" |
| 0.120" | 0.010"-0.02" | 0.25" |
| 0.180" | 0.012"-0.03" | 0.26" |
| 0.280" | 0.015"-0.05" | 0.27" |
| 0.400" | 0.020"-0.080" | 0.28" |
| 0.600" | 0.022"-0.100" | 0.30" |

The size of the slots 78 can be made with less metal removed for higher strength or more metal removed for greater flexibility. The dimensions of the cut width and length of the windows 78 can vary with the type of polymer material fused into the metal tube cuts 78 to form the composite reinforced tubing 12, for example, at the distal region 14. The wider the cut 78 the more polymer material that can flow through the windows 78 when melted under pressure. If the polymer material that encapsulating the laser cut metal tube is soft, such as between 20 Shore A and 35 Shore D durometers, then more flexibility is imparted to the composite tube 12 in the distal region 14. The cuts 78 can be smaller if the polymer encapsulating material is of a higher modulus or is otherwise stiffer. The composite tubing can be stiffer when a stiffer encapsulating material is used with the same sized windows. Therefore, with higher modulus materials such as 40D or higher, the window width can be increased to allow the stiffer, more viscous material to flow through the cuts 78 when molten and fully encapsulate the laser cut metal tube reinforcement 56.

FIG. 7d illustrates a variation the hypotube 56 of FIG. 7a in a flattened configuration. As shown, the width between the cuts 78 can be about 0.01". Other widths between the cuts 78, more or less, are also appreciated. In pattern 74, the cuts 78 can increment at a starting position that is indexed at a helix angle to create the compound bending curve in pattern 74.

A helical pattern of a laser cut tube (e.g., the helical pattern in zone 74 of hypotube 56) can be combined with other means to program the bending characteristics of the composite tubing 12 in the distal region 14. For example, in addition to the helical pattern, the polymer configuration can be arranged in such a way that a harder material, such as stainless steel or high durometer polymer, is adjacent to softer polymer material that is fused to the harder material by heat, pressure, chemical bond or a combination of all three. In such variations, the laser cut hypotube 56 can be replaced by a braid of relatively harder polymer or metal material to provide the torque and strength that prevent the tubing 12 from kinking or buckling during use. The laser cut hypotube can be replaced by a hard plastic or metal coil which can provide the strength to prevent the tubing from kinking or buckling while still allowing the tube 12 to be flexible. For example, the laser cut hypotube can be replaced by a hard plastic or metal coil if torque is not a requirement or otherwise a primary concern.

When there is a change in the axial stiffness or the resistance to compressive loading is variable along the length of the catheter tube 12, a bending moment is established upon the application of a compressive force. As described above, the compressive force can be provided by the actuation of one or more of the control elements (e.g., pull wires 30w and/or pull tubes 30t) and is resisted by the material composing the wall of the tubing 12 (e.g., including the distal region 14). The resistive force can be an equal and opposite force exerted by the pull wire 30w at the location of the pull wire structure (e.g., first and second pull wire rings 46a, 46b) along the entire catheter tube 12 until the point of pull wire crimp attachment 32.

As the catheter shaft 12 wall thickness is compressed, an undesired secondary effect can be that the secondary curve 18 (e.g., see FIG. 1) is activated by the tensioning of the distal pull wires 30 attached more distal than the proximal pull wire attachment to the catheter shaft 12. To address this, a combination of materials can be used to isolate the forces causing the bending moment to be directed (e.g., preferably directed) to the distal bending moment location rather than the secondary bending moment location (e.g., to the first deflection portion 14a rather than the second deflection portion 14b). For example, one or more incompressible materials can be arranged to provide column strength without drastically changing the resistance to lateral bending forces applied in a normal orthogonal direction to the catheter tube axis. As another example, a coil can be arranged over the laser cut hypotube 56 that has a dual bending moment pattern cut into it. The coil can be encapsulated or otherwise embedded in the wall of the tubing 12. The coil can be a close wound coil with zero gap between each wrap. The coil can be made of metal wire. The coil can end at a location adjacent to the proximal pull wire ring 46b such that when one of the distal pull wires 30w is tensioned, the location of bending moment is isolated to the end of the coil. The coil can be sufficiently flexible to not substantially increase resistance to lateral forces. The proximal pull ring portion of the catheter shaft 14b can be flexible and have the same axial stiffness as the more distal deflection segment 14a.

Hemostasis Valve

As described above with reference to FIG. 1, the catheter 10 can have one or more hemostasis valves 88. The one or more hemostasis valves 88 can prevent blood loss as devices are inserted into and/or removed from a patient's vasculature via the catheter 10. For example, the catheter 10 can have one, two, three, or more hemostasis valves. Other numbers of hemostasis valves 88, more or less, are also appreciated.

One or more of the one or more hemostasis valves 88 can be partly and/or entirely made of the fluoroelastomer/ePTFE composite material described above with reference to the shaft 12. For example, one or more portions of the one or more hemostasis valves 88 can be made of the fluoroelastomer/ePTFE composite material. The fluoroelastic and ePTFE composite material and the process for making it will be described in further detail below.

The combination of elasticity and low friction that this composite material provides can advantageously allow the hemostasis valves 88 to be passively and/or actively operated. The hemostasis valves 88 can be normally open and/or normally closed. The composite material can allow the valves 88 to seal around and/or against devices that occupy the valves 88 during insertion, during use, and/or during removal. The composite material can allow the valves 88 to stretch around and/or against devices that occupy the valves 88 during insertion, during use, and/or during removal.

The hemostasis valves 88 can be actuated, for example, when a user presses a button or otherwise actuates a mechanism on the handle 24 (and/or when the catheter 10 receives an auditory command). The valves 88 can open and/or close when activated. For example, for normally closed valves 88, the valves 88 can open when activated. For normally closed valves 88, the valves 88 can open when activated.

The hemostasis valves 88 can be passively actuated, for example, when a device is translated (e.g., pushed or pulled) through the valves 88. The low modulus of elasticity and low surface friction of the composite material can advantageously allow the valves 88 to be passively operated without being actively actuated via a control mechanism (e.g., a button).

The hemostasis valves 88 can be passively and actively actuated. Actively actuating the hemostasis valves 88 can reduce the forces that develop in the catheter system. For example, by pressing the button or actuator, the force applied by the elastomeric tubing is lessened to allow for the device to be inserted through the valve with less force. This can be important to avoid damage to certain easily damaged instruments when advancing through a passively activated valve 88.

One or more structures can be arranged to provide a releasable closing force directed on the outer surface of the fluoroelastomer valve 88 (e.g., for some radial distance). The closing force can be radially uniform force directed on the outer surface of the fluoroelastomer valve 88. For example, a spring tension-able strap can be used to provide a releasable radial force to the fluoroelastomer valve 88.

One or more of the fluoroelastomer valves 88 can be reinforced with braid elements or axially oriented elements to provide dynamic support while a device is being introduced through the valve. The reinforcing material can be nitinol wire, stainless steel, PEEK, oriented ePTFE, ETFE, EFEP, or other polymer or metal. This reinforced structure can form reinforcement tubing. The reinforcement tubing can have a normally open configuration with an adjustable closing force that can be applied by a spring tension-able strap, although any suitable closing force mechanism is appreciated. The variable tension strap can be activated to allow for the temporary opening of the valve 88, as well as to allow for an adjustable amount of closing force to be applied (e.g., by adjusting the amount of spring tension). Other structures that provide a closing force are also appreciated (e.g., see FIGS. 8a1-8/6). In this way, the valves 88 can be adjusted to provide a lessor or greater degree of sealing force and sliding resistance through the valve 88 than through conventional hemostasis valves. The hemostasis valves 88 give users greater control over the forces that develop between the valve, the catheter, and/or devices inserted into the catheter.

Any portion of any hemostasis valve, including the whole valve, can be made from the fluoroelastomer/ePTFE composite material.

FIGS. 8a1-8/6 illustrate variations of hemostasis valves 88 with a structure and/or mechanism capable of delivering a releasable closing force.

FIGS. 8a1-8a4 illustrate that the valves 88 can have an elastic tubing 90 configured to be disposed within a sleeve 92. The sleeve 92 can have a strap 94. The sleeve 92 can compress the elastic tubing 90 when, for example, the strap 94 is pulled. When the strap 94 is pulled, the diameter of the sleeve 92 can decrease, thereby decreasing the diameter of the tubing 90. As shown, the sleeve 92 shown in FIG. 8a1-8a4 can function like a "zip tie" in that the strap 94 can pass through an opening in an end of the sleeve 92 and be cinched closed when tightened. The elastic tubing 90 can be made from fluoroelastomer/ePTFE composite material and/or other suitable material such as silicone, polyurethane, chronoprene, rubber or other elastomers. Multiple sleeves 92 are shown in FIG. 8a2, for example, 2 to 10 or more sleeves (e.g., 6 sleeves 92 are shown in FIG. 8a2). A cross section of the strap 94 is illustrated in FIG. 8a4.

FIGS. 8b1-8b6 illustrate a loop 96 that can be disposed around the elastic tubing 90 of FIGS. 8a1-8a4. The loop 96 can compress the elastic tubing 90 when, for example, one or both ends of the loop 96 are pulled. When an end of the loop 96 is pulled, the diameter of the loop 96 can decrease, thereby decreasing the diameter of the tubing 90. As shown, two or more loops 96 can be combined together (e.g., see upper left, lower left, and lower right illustrations of FIG. 8b). Combining two or more loops 96 together can advantageously provide a wider width over which the tube 90 can be compressed. The multiple loops 96 can be cinched down over the tubing 90 to close the internal diameter by pulling on their ends to tighten the loop (e.g., see FIG. 8b5 showing a pre-cinched loop 96 having a length $l_2$ and a diameter $d_2$ being cinched to a post-cinched configuration having a length $l_1$ and a diameter $d_1$). The loops 96 can be cinched, for example, by pulling the length $l_2$ to length $l_1$ which decreases the diameter from $d_2$ to $d_1$. The diameter $d_1$ can be from about 0.02 inches to about 0.25 inches or more, including every 0.01 inch increment within this range (e.g., 0.05 inches). The diameter $d_2$ can be from about 0.20 inches to about 0.55 inches or more, including every 0.01 inch increment within this range (e.g., 0.40 inches). The length $l_1$ can be from about 1.00 inches to about 3.00 inches or more, including every 0.01 inch increment within this range (e.g., 2.00 inches). The length $l_2$ can be from about 0.30 inches to about 1.75 inches or more, including every 0.01 inch increment within this range (e.g., 0.90 inches). The loops 96 can be a wire, sting, strap, and the like.

FIGS. 8c1-8c7 illustrate variations of a strap 102, a securement loop 104, a securement structure 106, and a ring 108. Each of these can be used to decrease the diameter of tube 90 of FIGS. 8a1-8a4. The strap 102 can be a strip of material that is wider than a wire or string. For example, the strap 102 can have a width from about 0.1" to about 1.0," for example, from about 0.25" to about 0.5". Other widths, more or less, as well as other ranges, narrower or wider, are also appreciated. The strap 102 can be woven (e.g., like a seat belt). The strap 102 can be made from a variety of polymer materials, braided wire, and/or filament. The securement loops 104 can be used with the strap 102, or any other strap. The securement loops 104 can allow the strap 102 to be cinched down and reduce the internal diameter of the loop of strap 102. The securement structures 106 can have one or more holes and/or channels 107. For example, the securement structures 106 can have an array of holes/channels 107. The array of holes/channels can separate one or more filaments from one another when and can provide two ends of each string to pull. The filaments can be strings, wires, and the like. The ends of the filaments on one side of the array 107 can be pulled at the same time and the same rate as the ends of the filaments on the other side of the array 107. This can advantageously close down the internal diameter over a longer length of tubing 90 than a single loop of string which applies compression to the tubing at a single point of contact. Other arrays with different numbers of holes/channels are also appreciated. The ring 108 can allow the ends of one or more filaments to be pulled to reduce the internal diameter of the tube 90 when the strap 102 is looped around the circumference of the tube 90 and goes through the ring pulley 108.

FIGS. 8d1 and 8d2 illustrate a cross section of a variation of the valve 88 shown in FIG. 1 in an open configuration (FIG. 8d1) and in a closed configuration (FIG. 8d2). As shown, the handle 24 can have two buttons 110, 112 (also referred to as activation elements). Other numbers of buttons, more or less, are also appreciated. The two buttons 110, 112 can loosen and/or tighten one or more filaments against the tube 90, thereby increasing and/or decreasing the lumen of the tube 90. Two filaments (e.g., filament 96) are illustrated in FIGS. 8d1 and 8d2. The two filaments can loop around a portion of the circumference of the tube 10 (e.g., about half of the circumference) when the buttons are activated (shown, for example, by the facing arrows). The two filaments can loop around a portion of the circumference of the tube 10 (e.g., about half of the circumference) when the buttons are not activated (shown, for example, by the opposing arrows). As shown, the tube 90 can be in an open configuration when the buttons are in an activated position and a closed configuration when the buttons are in a non-activated position. The tube 90 can be closed by the strings when the buttons are in their non-activated positions (e.g., their outer positions). There can be a compression spring between the buttons 110, 112 and the housing of the handle 24 that can keep the buttons 110, 112 normally in the non-activated (e.g., outward position) so the tube 90 is normally closed. The amount of button travel can be about 0.5" for each button 110, 112. For example, to be activated from a non-activated position, the buttons 110, 112 can each travel about 0.5".

FIGS. 8d3-8d6 illustrate a variation of a braid 114. The braid 114 can be a wire braid, among any other type of braid. As shown, the wire braid 114 can have first and second lengths $l_1$, $l_2$ and can have first and second internal diameters $d_1$, $d_2$. The braid 114 can be made from nitinol or other shape change material. For example, the braid 114 can be heat shaped to normally be in a reduced diameter condition where $l_2$ is longer than $l_1$ and $d_2$ is less than $d_1$. When the braid length $l_2$ is compressed to $l_1$ the diameter $d_2$ can open to $d_1$. When the compressive force is removed, the diameter of the braid 114 can elastically return from $d_1$ to $d_2$. The tubing 90 can be in an open configuration when the braid length $l_2$ is compressed to $l_1$ and can be in a closed configuration when the compressive force is removed. The compressive force can be applied to the braid tubing structure 114 via an advancement mechanism (e.g., see FIGS. 8e1-8e6) attached to the braid 114.

FIGS. 8e1-8e6 illustrate a variation of an advancement mechanism 116. As shown in FIGS. 8e1 and 8e2, the advancement mechanism 116 can be a threaded hollow tube. As shown in FIGS. 8e3-8e6, the advancement mechanism 116 can be two inclined planes disposed for sliding motion.

FIGS. 8f1-8f6 illustrate that the valves 88 can have a braid 114 disposed over first and second support tubes 118, 120. The braid 114 can be a heat shaped wire braid. The tube 90 can be disposed within the braid 114. As shown, the wire braid 114 can have an open configuration and a closed configuration. The braid 114 can normally be in the closed configuration, for example, with an elongated length $l_1$. A cross section of the closed configuration is taken along the line A-A (see FIG. 8f5). When the two support tubes 118, 120 are brought closer together, the braid 114 can transition from a closed configuration to an open configuration and releases its compressive force on the internal diameter in which has the tube 90 disposed within, thereby expanding the tube 90 from a closed configuration to an open configuration. When compressed, the wire braid 114 can naturally have a restoration force that is opposed by the inclined plane buttons 116 and/or the threaded hollow tube pusher 116. FIGS. 8f1-8f6 further illustrate that angle α can be greater than angle β. The diameter $d_1$ can be less than the diameter $d_2$. For example, the diameter $d_1$ can be from about 0.00 inches to about 0.25 inches or more, including every 0.01 inch increment within this range (e.g., 0.00 inches). The diameter $d_2$ can be from about 0.10 inches to about 0.55 inches or more, including every 0.01 inch increment within this range (e.g., 0.50 inches). The length $l_1$ can be from about 1.00 inches to about 3.00 inches or more, including every 0.01 inch increment within this range (e.g., 1.50 inches). The length $l_2$ can be from about 0.30 inches to about 1.75 inches or more, including every 0.01 inch increment within this range (e.g., 1.00 inches).

Catheter and Components

Figure 9:
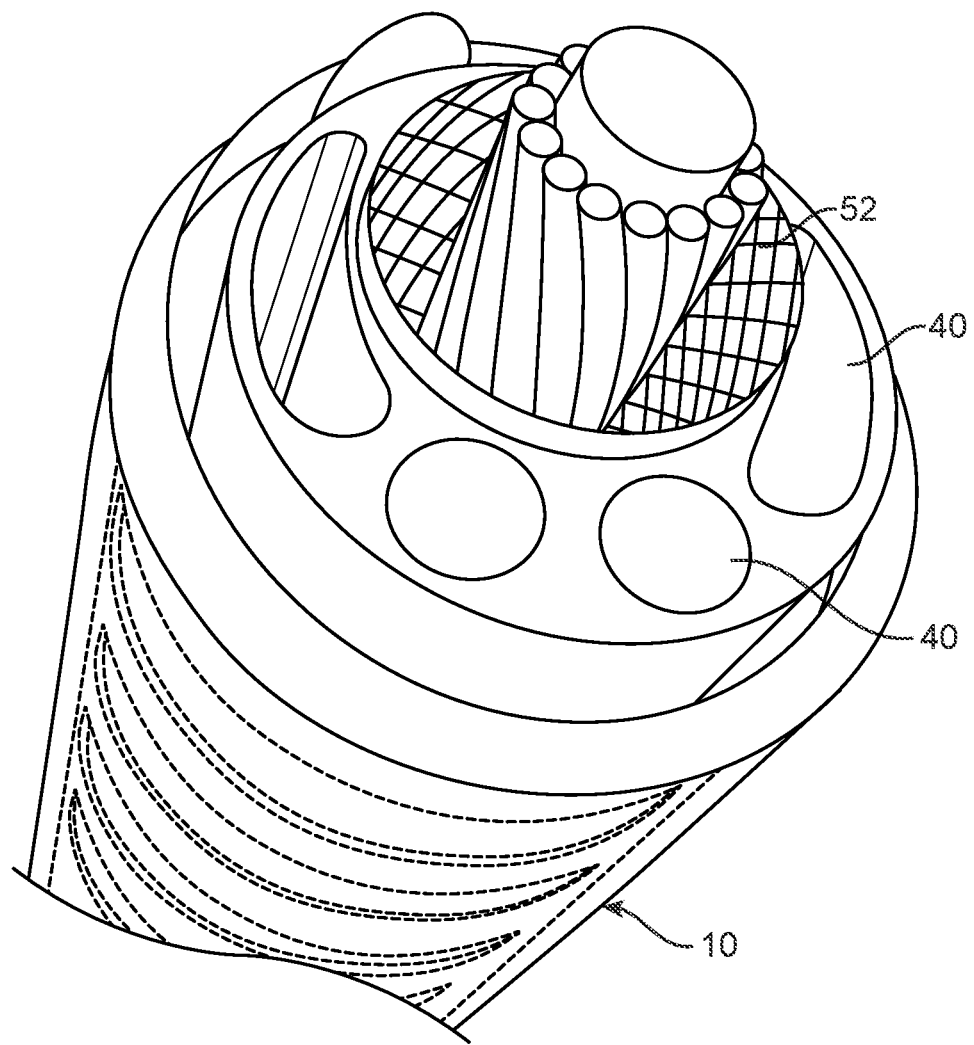
FIG. 9 illustrates a variation of a deflectable catheter.

FIG. 9 illustrates a variation of the catheter 10 having a braid 52 and lumens 40. The catheter 10 can be reusable. The catheter 10 can be a steam sterilizable polymer device. The catheter 10 can have a 60 Shore A Hardness, a low coefficient of friction, chemical resistance and thermal stability.

FIGS. 10a1 and 10a2 illustrates two variations of tubes 56 (e.g., laser cut hypotubes).

FIG. 10b illustrates that the tube 56 can have a jacket 128 of material around the tube 56.

FIG. 10c illustrates that a pull wire 30w can exit a lumen of the deflectable catheter 10, for example, at a skived proximal pull wire exit lumen of the catheter 10. The pull wire can exit the lumen in the deflectable region 14, in another deflectable region, or in a non-deflectable region of the catheter 10.

FIG. 10d illustrates that the catheter 10 can have a liner 132. For example, FIG. 10d illustrates that the catheter 10 can have a coil reinforced catheter tip with PTFE liner throughout.

FIG. 10e illustrates that the catheter 10 can have a multi-durometer shaft with variable stiffness. For example, FIG. 10e illustrates that the shaft 10 can have a first stiffness in a first region 134a and a second stiffness in a second region 134b, where the first and second stiffness are different from one another (e.g., greater in region 134a than in region 134b, or vice versa). The stiffness can change abruptly or gradually between first and second regions 134a, 134b.

The jacket 128 and liner 132 materials can be, for example, FEP, PTFE, ePTFE, PEBA, PEBASLIX, FLUROSLIX, NYLOSLIX, HDPE, polyurethane, or any combination thereof.

The braid and coil materials can be round and/or flat stainless steel wire, nitinol, PEEK, aramid fiber, LCP, PEN, and others.

The catheters 10 can be manufactured with color matching to according to customer specifications.

The catheter 10 can have one or multiple radiopacity features, for example, embedded marker bands, embedded radiopaque stripes, a metallic and/or compounded polymer tip (e.g., PT/IR, tungsten, BaSO4, bismuth subcarbonate), or any combination thereof.

Figure 11C:
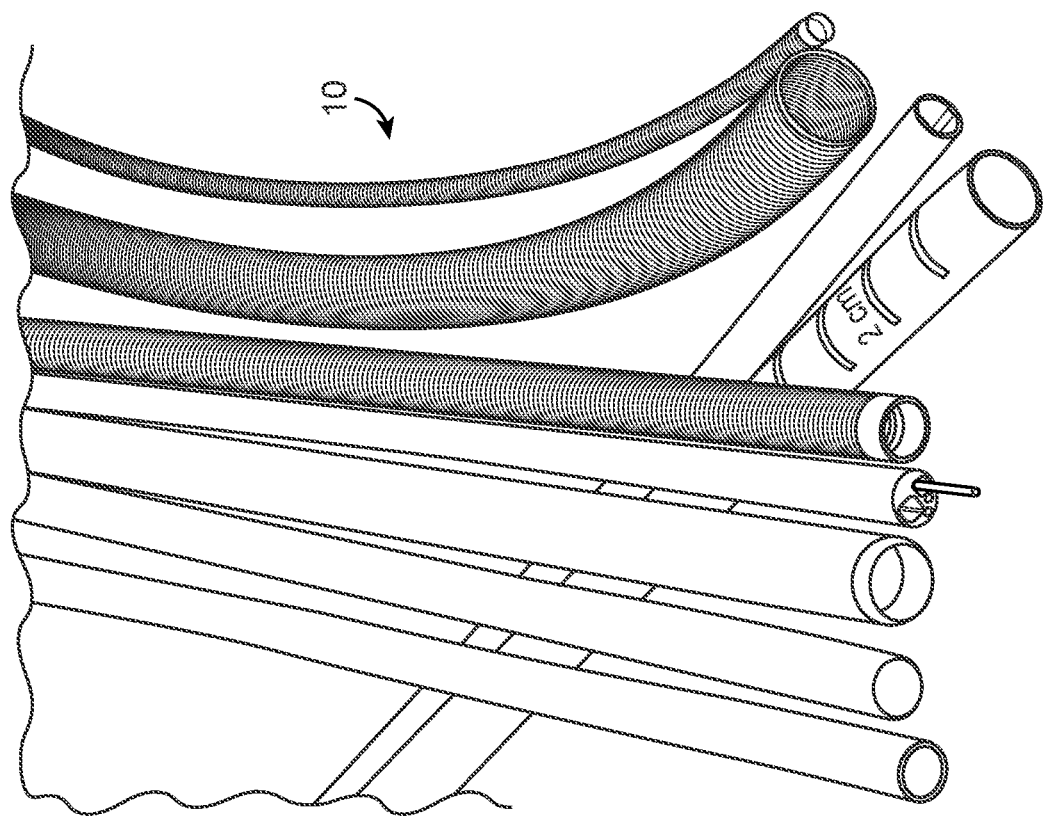
FIG. 11c illustrates variations of various tube components of a catheter.
Figure 11B:
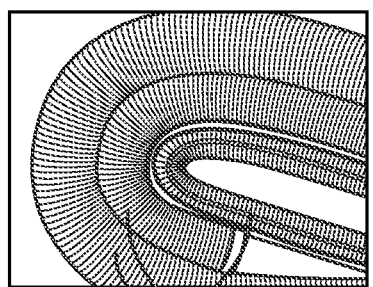
FIG. 11b illustrates variations of catheters in an exemplary deflected configuration.
Figure 11A:
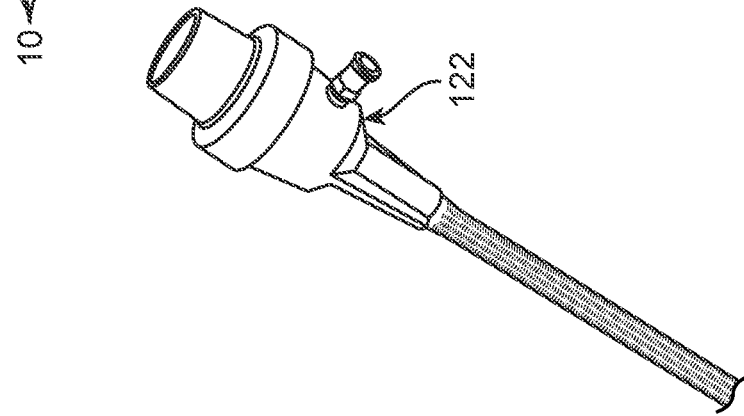
FIG. 11a illustrates a variation of a hemostasis valve.

FIG. 11a illustrates that a hemostasis valve 122 having a flush port can be integrated with the catheter 10. The valve 122 can be an active or a passive valve.

FIG. 11b illustrates catheters 10 in a deflected configuration having a bend radius. The catheters 10 can be constructed with a stainless steel coil, laser cut hypotube, braids, or any combination thereof.

FIG. 11c illustrates various tube components of the catheter 10.

Composite Material

As described above, one or more components of the catheter 10 can be partly and/or entirely made a fluoroelastic and ePTFE composite material. For example, the shaft 12 can be made partly and/or entirely from the fluoroelastomer and ePTFE combination. As another example, one or more of the one or more hemostasis valves 88 can be made partly and/or entirely from the fluoroelastomer and ePTFE combination. As yet another example, one or more telescopic catheter shafts of a telescopic catheter system can be made partly and/or entirely form the fluoroelastomer and ePTFE combination.

The composite material can be formed by combining TFE molecular chains of a thermoplastic fluoroelastomer with TFE molecular chains of unsintered, partially sintered, and/or fully sintered ePTFE using, for example, a thermal fusion process.

Within the group of fluoroelastomers that are commercially available, there are melt process-able thermoplastic grades as well as liquid cured two component grades such as neoprene, which is a thermoset material once the components have cured through a chemical reaction, usually in the presence of a catalyst. Thermoset fluoroelastic materials do not exhibit melting behavior upon reheating to elevated temperatures. By contrast, melt process-able fluoropolymers can melt upon reheating and provide molecular chain mobility. The TFE chains of a melt process-able fluoroelastomer can be fused at the molecular level by chain entanglement and creation of new bonds where the input thermal energy can allow for energetically favorable bonds to form with compatible chains of ePTFE. The TFE molecular chains of a thermoplastic fluoroelastomer can be fused with the TFE molecular chains of ePTFE when, for example, the materials are subject to a sufficient compressive force and the temperature is above the melting point of the fluoroelastomer.

The method of combining these two materials, which is described partly above and more below, can impart a low modulus and a low coefficient of friction to the material. For example, the method can impart low friction properties to the joined surfaces of the two materials and not homogeneously throughout the resultant composite material. For example, the composite material can have a different molecular structure at the surface than in the center of the wall of the composite material.

The composite fluoroelastomer/ePTFE material can be fused together such that it does not delaminate or separate into its components layers when high strain is applied to the composite material over multiple cycles. This property along with the ability to thermally reflow the material to encapsulate or otherwise embed reinforcement materials and/or structures makes the fluoroelastomer/ePTFE composite material well-suited for the construction of deflectable catheter and endoscopic tubing, as well as for other components and devices. For example, as described above, reinforcement structures such as wire, metallic fibers, polymeric fibers and/or mesh can be embedded into the fluoroelastomer/ePTFE composite material. As described above, the composite material can be stable at temperatures above steam autoclaving temperatures, and can be highly chemical resistant, allowing for the re-sterilization of devices such as endoscopic and/or catheter tubing made of this material.

Various steps of a variation of a thermal fusion process for making the fluoroelastomer and ePTFE combination are below. The steps can be performed in any order.

1. Extrude thermoplastic fluoroelastomer as a tubing (although other forms are possible, e.g., a film or a rod, among others).
2. Place ePTFE tubing on a mandrel (e.g., solid round, shaped profile, or tube) made from stainless steel or other metal.
3. Place thermoplastic elastomer over ePTFE tubing.
4. Insert an additional tube of ePTFE on top of the thermoplastic elastomer.
5. Insert a high temperature heat shrink material such as PTFE over the assembly. PTFE heat shrink with a recovery ratio of at least 1.1:1, for example, 4:1 or higher. Other recovery ratios, more or less, are also appreciated.
6. Heat the assembly either through a lamination process where heat is applied to one end of the assembly and the heat is translated across the length of the assembly. The temperature of the lamination process can range from 450 degrees Fahrenheit to 720 degrees Fahrenheit, for example, 600 degrees Fahrenheit. Other temperatures, more or less, as well as other ranges, narrower or wider, are also appreciated. The amount of pressure applied by the heat shrink can be applied in other ways such as compression from a silicone elastomer tubing that is used to apply the pressure required under heat. As another example, a metal mold can be used to apply the required pressure at elevated temperature. Pressures of at least 1 psi should be used. For example, the pressure can range from 100 psi to 2000 psi.
7. Alternatives to lamination can achieve the same result. For example, rather than moving heat across the part, the fusing or laminating of the components can be done using an oven to heat the entire assembly at the same time.

Various steps of a variation of a thermal fusion process for making the fluoroelastomer and ePTFE combination are below. The steps can be performed in any order.

1. Extrude ePTFE.
2. Overjacket the thermoelastomer on top so that the internal diameter is ePTFE (composite liner).
3. Using a continuous lamination process, apply the ePTFE to the outside of the composite by wrapping ePTFE on the outer diameter while the composite liner is supported by a mandrel, or by inflating the inner composite liner to expand up to the internal diameter of the outer tube of ePTFE. This process and diameter of the final outer diameter can be controlled by a die which restricts the diameter from growing while under pressure and heat. The die can be a long tube so that the pressure is maintained by the outer glass or metal tubing (long tube sizing die) until the temperature away from the lamination area is sufficiently cool so that the material no longer needs support while under pressure.
4. The advantage of this method is that there is no need for heat shrink materials to perform the process. This can save costs by eliminating the heat shrink material from the process, which is removed after lamination, as well as by reducing the handling and assembly time. Using the over jacket method, an ePTFE extrusion is brought through the extruder crosshead where the molten fluoroelastomer is brought into contact with the ePTFE. The crosshead can have the temperature and pressure required to perform the fusing of the two materials. This method has the advantage of being able to be performed in a continuous manner as opposed to discrete lengths.

The duration of thermal fusing can be short. For example, in a lamination process using heat shrink the rate of thermal traverse can be in the range of 0.2 inches/minute to 20 inches/minute. The rate of thermal traverse can be dependent upon the type of heat transfer method, such as radiant heat, pressurized hot air, convection, contact die, heater band, or other as well as the size and volume of the product being fused. For example, a suitable rate for a tubing of 0.250" diameter and 0.020" wall thickness can be two inches per minute with hot air nozzle operating at 5-10 cfm. In an oven the assembly, the required fusing temperature must exist at the interface of the fusion materials. This can take 30 seconds to 1 hour or more. In the overjacketing extrusion process, the extrusion line speed can range from 3 ft/min to 200 ft/min, for example, 10 ft/min to 60 ft/min. Other ranges and values than those above are appreciated.

The appendices below are part of this provisional application.

Like reference numerals in the drawings indicate identical or functionally similar features/elements.

All dimensions disclosed herein are exemplary. The dimensions disclosed herein can at least be expanded to ranges from about 50% to about 150% of the exemplary dimension shown herein, more narrowly from about 75% to about 125% of the exemplary dimension shown herein. Language such as "at least," "greater than," "less than," "between," and the like includes the number recited.

The words "may" and "can" are interchangeable (e.g., "may" can be replaced with "can" and "can" can be replaced with "may").

Any elements described herein as singular can be pluralized (e.g., anything described as "one" can be more than one, anything referred to with an indefinite article, e.g., "a" or "an," can be more than one, anything referred to with the definite article "the" can be more than one, etc.).

Any species element of a genus element can have the characteristics or elements of any other species element of that genus.

The above-described and illustrated features, elements, configurations, assemblies, sub-assemblies, complete assemblies, and/or methods and their elements for carrying out the invention can be combined and/or modified with each other in any combination.

Any of the below claims and/or variations can be combined and/or modified with each other in any combination, as well as combined and/or modified with any other portion of the disclosure in any combination. The below claims are exemplary and not limiting.

The invention claimed is:

1. A deflectable tip catheter comprising:
   a first deflection region operably deflectable into a first curve via a first control element; and
   a second deflection region operably deflectable into a second curve via a second control element,
   wherein the first control element is in a lumen of the second control element distal a handle of the deflectable tip catheter,
   wherein a width of the lumen of the second control element is less than a thickness of a wall of a shaft of the deflectable tip catheter,
   wherein the first deflection region is distal the second deflection region,
   wherein the first deflection region is independently deflectable relative to the second deflection region,
   wherein the second deflection region is independently deflectable relative to the first deflection region, and
   wherein a deflection bending moment of the first deflection region is isolated from the second deflection region such that the deflection bending moment of the first deflection region is preferentially applicable to the first deflection region.

2. The deflectable tip catheter of claim 1, wherein the first deflection region comprises a fluoroelastomer composite material fused with expanded polytetrafluoroethylene (ePTFE), wherein the second deflection region comprises a fluoroelastomer composite material fused with expanded polytetrafluoroethylene (ePTFE), and wherein the deflectable tip catheter further comprises a hemostasis valve comprising a fluoroelastomer composite material having expanded polytetrafluoroethylene (ePTFE).

3. The deflectable tip catheter of claim 1, wherein the first deflection region is deflectable into the first curve when the second deflection region does not have the second curve,
   wherein the first deflection region is deflectable into the first curve when the second deflection region has the second curve,
   wherein the second deflection region is deflectable into the second curve when the first deflection region does not have the first curve, and
   wherein the second deflection region is deflectable into the second curve when the first deflection region has the first curve.

4. The deflectable tip catheter of claim 1, wherein when the first deflection region is deflected into the first curve and when the second deflection region is deflected into the second curve, the first curve and the second curve are two segments of a single curve.

5. The deflectable tip catheter of claim 4, wherein when the first deflection region is deflected into the first curve and when the second deflection region is deflected into the second curve, the first curve has a first radius of curvature and the second curve has a second radius of curvature, and wherein the first radius of curvature is the same as or different than the second radius of curvature.

6. The deflectable tip catheter of claim 1, wherein when the first deflection region is deflected into the first curve and when the second deflection region is deflected into the second curve, the first curve and the second curve are two segments of a compound curve.

7. The deflectable tip catheter of claim 1, wherein the first deflection region abuts the second deflection region, wherein the shaft comprises a first layer, a second layer, and a third layer, wherein the second layer is between the first layer and the third layer, and wherein at least one of the first layer, the second layer, and the third layer comprises a fluoroelastomer composite material fused with expanded polytetrafluoroethylene (ePTFE).

8. The deflectable tip catheter of claim 1, wherein a catheter section is between the first deflection region and the second deflection region, wherein the catheter section between the first deflection region and the second deflection region comprises a third deflection region operably deflectable into a third curve, and wherein the third deflection region is independently deflectable.

9. The deflectable tip catheter of claim 1, wherein the shaft comprises a composite tube comprising a first tube and a second tube, wherein the first tube comprises expanded polytetrafluoroethylene (ePTFE) and the second tube comprises a fluoroelastomer, wherein the first tube is fused with the second tube, and wherein the first tube is inside the second tube.

10. The deflectable tip catheter of claim 1, further comprising a first control and a second control, wherein the second control is on opposite lateral sides of the first control, and wherein the first control is longitudinally moveable inside the second control.

11. The deflectable tip catheter of claim 1, wherein the shaft comprises a composite tube comprising a first tube and a second tube, wherein the first tube comprises expanded polytetrafluoroethylene (ePTFE) and the second tube comprises a fluoroelastomer.

12. The deflectable tip catheter of claim 1, wherein the first control element is longitudinally moveable in the lumen of the second control element.

13. The deflectable tip catheter of claim 1, wherein the first control element and the second control element are in a lumen in the wall of the shaft of the deflectable tip catheter, and wherein the lumen of the second control element is smaller than the lumen in the wall of the shaft.

14. The deflectable tip catheter of claim 1, wherein the first control element comprises a wire, and wherein the second control element comprises a tube.

15. The deflectable tip catheter of claim 1, wherein the first control element comprises a wire, and wherein the second control element comprises a flat structure.

16. The deflectable tip catheter of claim 1, wherein the first control element comprises a wire, and wherein the second control element comprises a flat wire braid or a woven tape.

17. The deflectable tip catheter of claim 1, wherein the lumen of the second control element has a diameter.

18. The deflectable tip catheter of claim 1, wherein the lumen of the second control element has a circular cross section.

19. The deflectable tip catheter of claim 1, wherein the first control element is movable in the lumen of the second control element.

20. The deflectable tip catheter of claim 19, wherein the second control element is movable over the first control element.

21. The deflectable tip catheter of claim 1, wherein when the deflectable tip catheter is in a straight configuration, a center longitudinal axis of the first control element and a center longitudinal axis of the second control element are offset from a center longitudinal axis of the deflectable tip catheter.

22. A deflectable tip catheter comprising:
a first deflection region operably deflectable into a first curve via a first control element; and
a second deflection region operably deflectable into a second curve via a second control element,
wherein the second control element comprises a lumen movable in a shaft of the deflectable tip catheter,
wherein when the deflectable tip catheter is in a straight configuration, a center longitudinal axis of the first control element and a center longitudinal axis of the second control element are offset from a center longitudinal axis of the deflectable tip catheter,
wherein the first deflection region is distal the second deflection region,
wherein the first deflection region is independently deflectable relative to the second deflection region, and
wherein the second deflection region is independently deflectable relative to the first deflection region.

23. The deflectable tip catheter of claim 22, wherein the shaft comprises a composite tube comprising a first tube and a second tube, wherein the first tube comprises expanded polytetrafluoroethylene (ePTFE) and the second tube comprises a fluoroelastomer, wherein the first tube comprises an inner layer of the composite tube and the second tube comprises an outer layer of the composite tube, and wherein the first tube and the second tube are fused together.

24. The deflectable tip catheter of claim 22, wherein the first control element is movable in the lumen of the second control element.

25. The deflectable tip catheter of claim 24, wherein the second control element is movable over the first control element.

26. The deflectable tip catheter of claim 25, wherein the first control element and the second control element are in a lumen in a wall of the shaft of the deflectable tip catheter, and wherein the lumen of the second control element is smaller than the lumen in the wall of the shaft.

27. The deflectable tip catheter of claim 24, wherein the first control element and the second control element are in a lumen in a wall of the shaft of the deflectable tip catheter, and wherein the lumen of the second control element is smaller than the lumen in the wall of the shaft.

28. The deflectable tip catheter of claim 22, wherein the first control element comprises a wire, and wherein the second control element comprises a tube or a flat structure.

29. The deflectable tip catheter of claim 22, wherein the lumen of the second control element is round.

30. The deflectable tip catheter of claim 22, wherein the second control element extends around the first control element.

31. The deflectable tip catheter of claim 22, wherein the first deflection region is deflectable into the first curve when the second deflection region does not have the second curve,
wherein the first deflection region is deflectable into the first curve when the second deflection region has the second curve,
wherein the second deflection region is deflectable into the second curve when the first deflection region does not have the first curve, and
wherein the second deflection region is deflectable into the second curve when the first deflection region has the first curve.

32. The deflectable tip catheter of claim 22, wherein when the first deflection region is deflected into the first curve and when the second deflection region is deflected into the second curve, the first curve and the second curve are two segments of a single curve.

33. The deflectable tip catheter of claim 32, wherein when the first deflection region is deflected into the first curve and when the second deflection region is deflected into the second curve, the first curve has a first radius of curvature and the second curve has a second radius of curvature, and wherein the first radius of curvature is the same as or different than the second radius of curvature.

34. The deflectable tip catheter of claim 22, wherein when the first deflection region is deflected into the first curve and when the second deflection region is deflected into the second curve, the first curve and the second curve are two segments of a compound curve.

35. The deflectable tip catheter of claim 22, wherein the shaft comprises a composite tube comprising a first tube and a second tube, wherein the first tube comprises expanded polytetrafluoroethylene (ePTFE) and the second tube comprises a fluoroelastomer.

36. The deflectable tip catheter of claim 22, wherein a width of the lumen of the second control element is less than a thickness of a wall of the shaft of the deflectable tip catheter.

37. The deflectable tip catheter of claim 36, wherein the first control element is in the lumen of the second control element distal a handle of the deflectable tip catheter.

\* \* \* \* \*